(12) United States Patent
Danilevskaya et al.

(10) Patent No.: US 7,763,778 B2
(45) Date of Patent: Jul. 27, 2010

(54) DELAYED FLOWERING TIME GENE (DLF1) IN MAIZE AND USES THEREOF

(75) Inventors: Olga Danilevskaya, Johnston, IA (US); Michael Muszynski, Johnston, IA (US); Bailin Li, Hockessin, DE (US); Thao Dam, Bear, DE (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 694 days.

(21) Appl. No.: 11/624,807

(22) Filed: Jan. 19, 2007

(65) Prior Publication Data
US 2007/0256198 A1 Nov. 1, 2007

Related U.S. Application Data

(60) Provisional application No. 60/760,839, filed on Jan. 20, 2006.

(51) Int. Cl.
C12N 15/29 (2006.01)
C12N 15/82 (2006.01)
C12N 15/87 (2006.01)
A01H 5/00 (2006.01)
A01H 5/10 (2006.01)

(52) U.S. Cl. .................. 800/298; 800/278; 800/290; 800/320; 800/320.1; 536/23.1; 536/23.6; 435/320.1; 435/410

(58) Field of Classification Search ............ None
See application file for complete search history.

(56) References Cited

U.S. PATENT DOCUMENTS

2003/0101479 A1* 5/2003 Cheikh et al. ............... 800/278

OTHER PUBLICATIONS

Larkin et al (1994, The Plant Cell 6:1065-1076).*
Muszynski, M., et al.; "Cloning of delayed flowering 1 (dlf1) gene from maize"; Plant Physiology (Dec. 2006) 142:1523-1536; American Society of Plant Biologists; Rockville, MD US.
Chardon, F., et al.; "Genetic Architecture of Flowering Time in Maize as Inferred From Quantitative Trait Loci Meta-analysis and Synteny Conservation With the Rice Genome"; Genetics (Dec. 2004) 168;2169-2185; Genetics Society of America; Bethesda, MD US.

* cited by examiner

*Primary Examiner*—Stuart F. Baum
(74) *Attorney, Agent, or Firm*—Pioneer Hi-Bred Int'l, Inc

(57) ABSTRACT

An isolated polynucleotide encoding a delayed flowering gene (DLF1) is provided, as is the isolated DLF1 protein, peptide portions thereof, and functional fragments of the DLF1. Also provided is a transgenic plant, which contains in its genome a transgene containing the polynucleotide encoding the DLF1 protein, or a nucleotide sequence complementary to the encoding polynucleotide. In addition, methods of identifying a nucleotide sequence and/or a heterologous protein that is specifically bound by the DLF1 protein, methods of using the isolated polynucleotide (or encoded polypeptide), for example, to modulate plant cell growth and/or development, are provided.

12 Claims, 10 Drawing Sheets

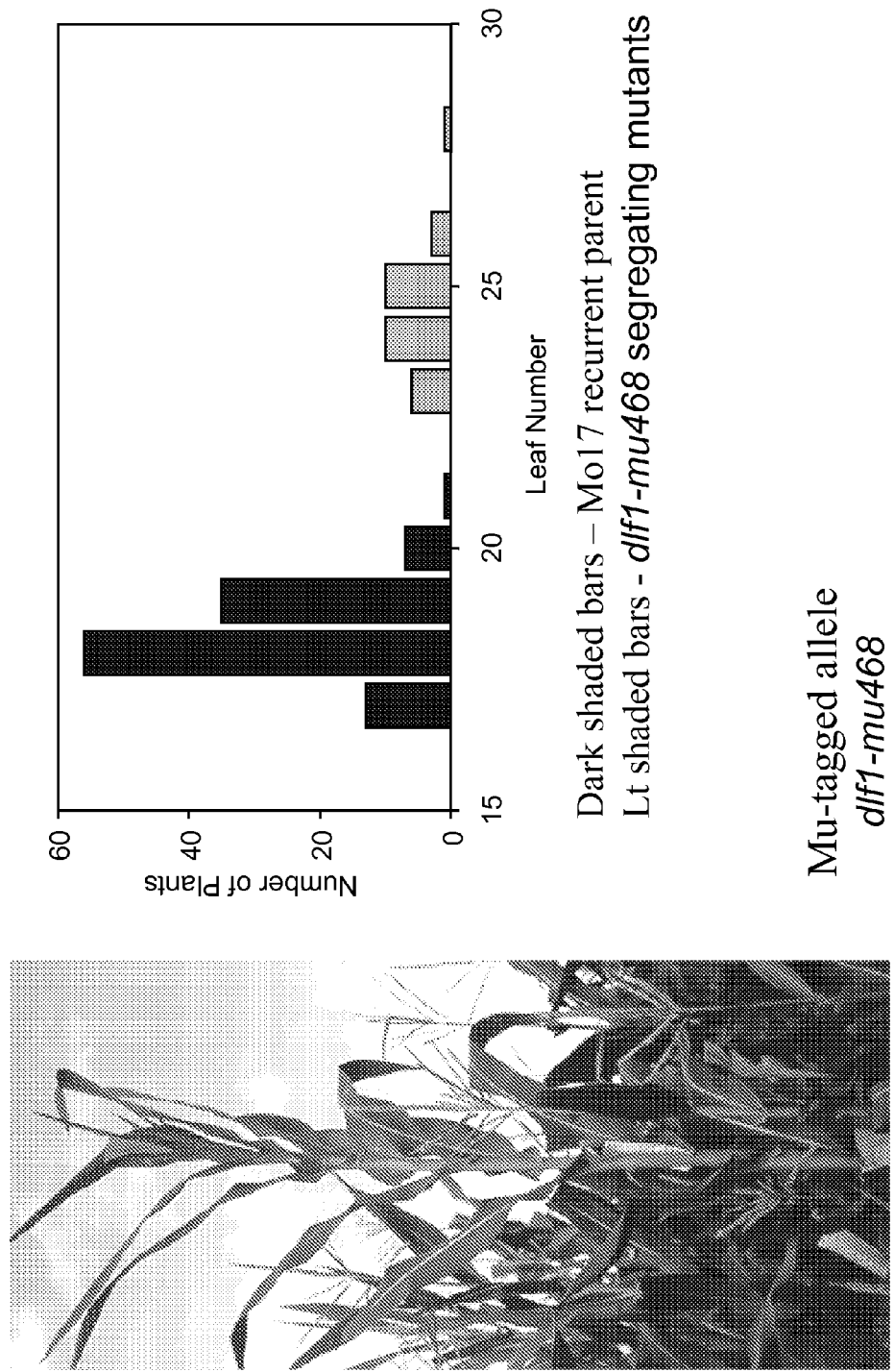
Figure 1. *DLF1* mutant phenotype

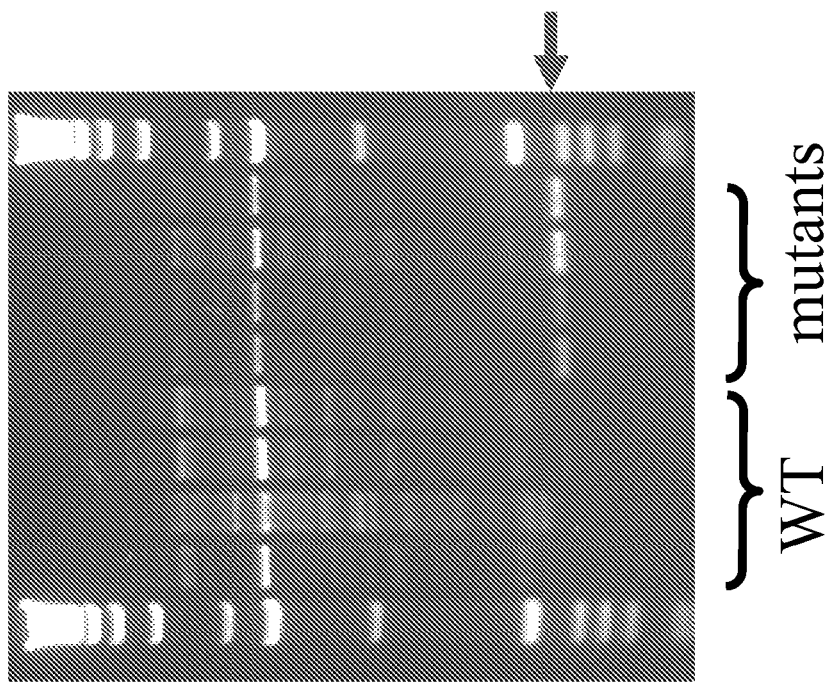
Figure 2 Segregation analysis of Mu-tagged *dlf-468* allele

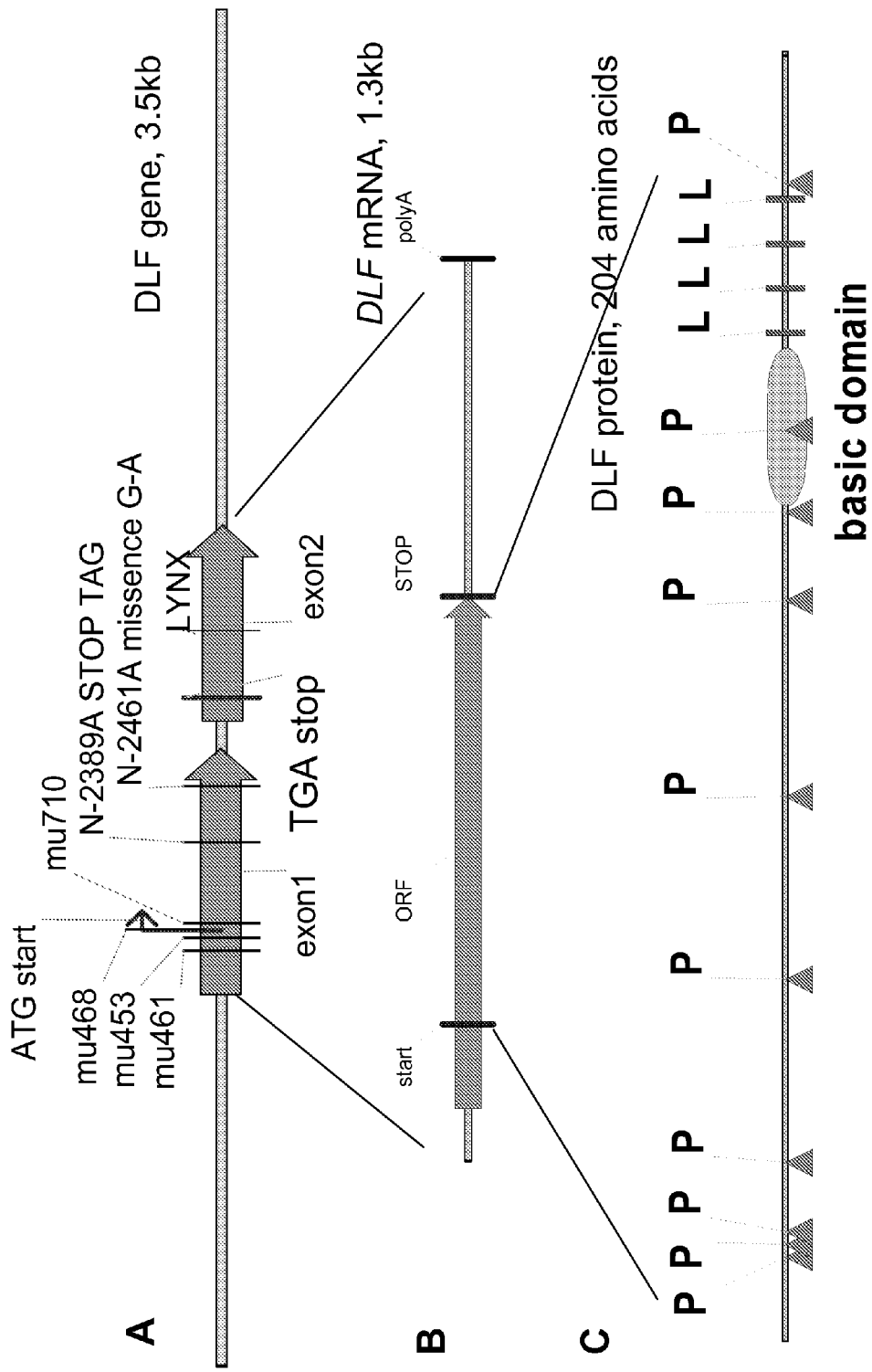
Figure. 3 *DFL1* gene, mRNA and protein structures

Figure 4. Protein alignment of the DLF wild type protein, and reference EMS N2461 missense and N2389A nonsense mutants

| | | |
|---|---|---|
| SEQ ID NO: 34 | (1) | MEDDEDIWANTASSPSASPPQFVAAGSVSTCSAFISTQLSLNSRLHLLSS |
| SEQ ID NO: 3 | (1) | MEDDEDIWANTASSPSASPPQFVAAGSVSTCSAFISTQLSLNSRLHLLSS |
| SEQ ID NO: 35 | (1) | MEDDEDIWANTASSPSASPPQFVAAGSVSTCSAFISTQLSLNSRLHLLSS |
| | | 51                                            100 |
| SEQ ID NO: 34 | (51) | AAAGGGSSPVRGAYGADGVRHHMALGGGFRNAAAS◊ |
| SEQ ID NO: 3 | (51) | AAAGGGSSPVRGGAYGADGVRHHMALGGGFRNAAASQPFFFYNLAGAG |
| SEQ ID NO: 35 | (51) | AAAGGGSSPVRGGAYGADGVRHHMALGGGFRNAAASQPFFFYNLAGAG |
| | | N2389A stop                         N2461 |
| SEQ ID NO: 3 | (101) | ADVEPFDGGRGVLEDDMSVGAAASGTWAGGGTDRRKKRMIKRESAARSR |
| SEQ ID NO: 35 | (101) | ADVEPFDGGRGVLEDDMSVGAAASGTWAGGGTDRRKKRMIKHESAARSR |
| | | 101                                          150 |
| SEQ ID NO: 3 | (151) | ARKQAYYPEIFTKVQIIQQENESLRVKYDELRESYEAVPMVPKTLQRMP |
| SEQ ID NO: 35 | (151) | ARKQAYYPEIFTKVQIIQQENESLRVKYDELRESYEAVPMVPKTLQRMP |
| | | 151                                          200 |
| SEQ ID NO: 3 | (201) | SAPF |
| SEQ ID NO: 35 | (201) | SAPF |

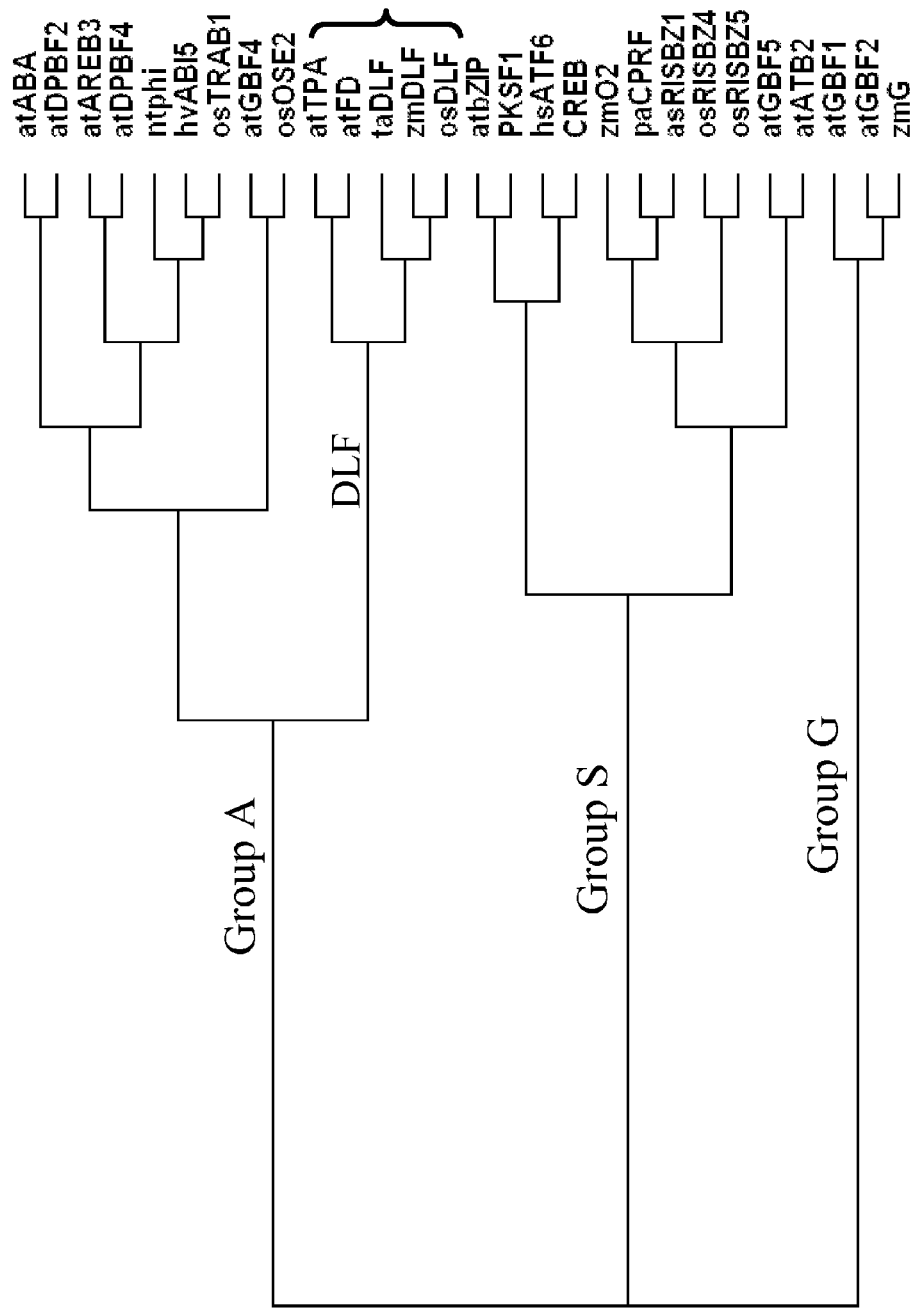
Figure 5. Phylogenetic tree of plant bZIP proteins defining the DLF family

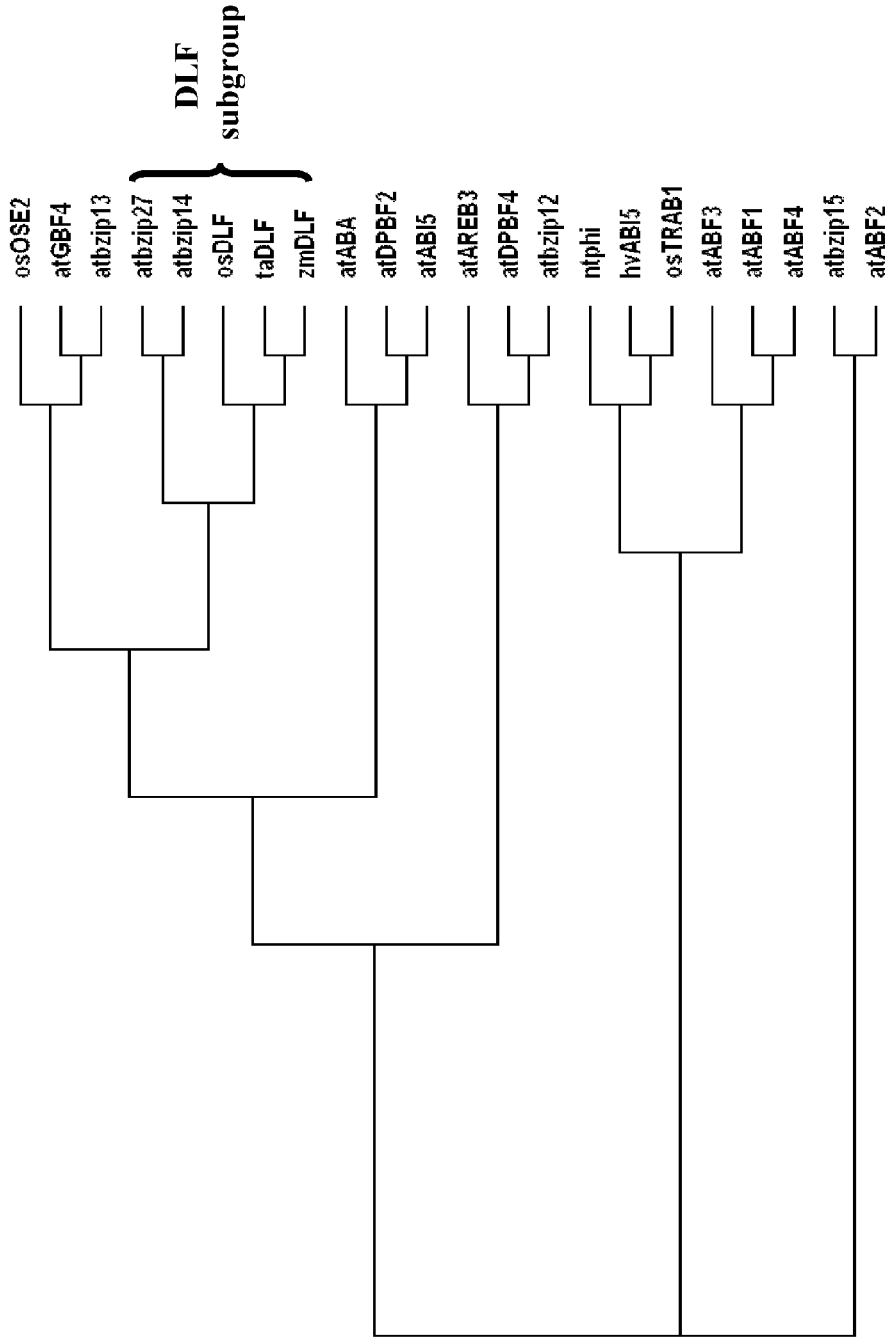
Figure 6. Phylogenetic tree of the group A of bZIP proteins

Figure 7. The amino acid alignment of proteins from the DLF1 clade

M1, Serine rich domain

DNA binding basic domain

Z – leucines forming "leucine zipper"

```
                        1                                                  50
SEQID NO:38   (1)   MLSSAKHQRNHRLSATNKNQTLTK VSSISSSSPSSSSSSTSSSSLPS------
SEQID NO:39   (1)   MLSSAKHN---------------- KINNHSAFSISSSSSSLSTSSS------
SEQID NO:36   (1)   ------------------------ MEDEDMVA ITS -SPSASPPRP------
SEQID NO:37   (1)   ------------------------ MAMEADDDPLW AVTTSPSASPPP------
SEQID NO:3    (1)   ------------------------ MEDEDIMA TASSPSASPPQPVAA
                        M1                                              100
                        51
SEQID NO:38  (51)   QDSQAQKR SLVTME EVWNDINLASTHHLNRH PHPQHNHEPRFRGQNHHN
SEQID NO:39  (31)   ---LGHNK SQVTME EVWKEINLGSLHYHRQL N-----IGHEPMLK-----N
SEQID NO:36  (22)   ---RSFT TAISINSTHLQGLLPSSFVD AAAS-----------------N
SEQID NO:37  (25)   -PSS--AAA TAISINTRLQILAATGVGGG ---------------------
SEQID NO:3   (26)   GSVSTCS SFTTQISINSRLHLLSSAAAGGG S--------------------
                        101                             M3              150
SEQID NO:38 (101)   QNPN-SIFQD FLKGSLNQEPAPTSQ -TTGSAPMGDSTHVTVLY-SSPFPP
SEQID NO:39  (69)   QNPNNSIFQD FLNMPLNQ-PPPPP -P--PPSSSTIVTIALYGSLPLPP
SEQID NO:36  (51)   -------- FCHASGNNN----- GGDGRNAAPMSSIFFALASYHQ
SEQID NO:37  (54)   -------- PHPCGYSAGSPFHP --GGGCYRGGASPTSFFSH--AAAS
SEQID NO:3   (59)   VRGGSKYGAADGVRHHHMAL GEGFFRMELASQGPFT PYNLAGA
                        151    M4                                       200
SEQID NO:38 (148)   PATLSLNSAGPEFLDNQDPLVTSNSNLHTHHHLSNAHAFNTSFEALVP
SEQID NO:39 (112)   PATYLSLNSCVHFEFLDTTENLLASNP----R------S---FEESAK
SEQID NO:36  (83)   QQHHLPLPAPLDCAI LPARRFG LD-------------------------
SEQID NO:37  (91)   FPRIASVDL PARRAIEREMCYGHGAA-----------------------
SEQID NO:3  (100)   GADVELFDGG --RGVLEDDMSVG--------------------------
                        201                                             250
SEQID NO:38 (198)   SSSFLKKRGQDSNE SSQNREKRMIKNEESA SRSRARKQA TTEELEYA
SEQID NO:39 (147)   FGCLGKKRGQDSDD TRGDERYKFMIKNEESA KSRSRKQA ISREELEZA
SEQID NO:36 (107)   -MCAA-AAPAGVP EAGDREKRMIKNEESA KSRSRARKQA RVNMETELE
SEQID NO:37 (118)   -AWPGLPGAGGGAAA PVDREKKRMIKNEESA SRSRARKQA HVTQIESEVH
SEQID NO:3  (121)   ----AAASGTWAGGGTD REKKRMIKNEESA RLSRSARKQA YVRELETKVQ
                        251                M5                        Z 300
SEQID NO:38 (248)   HLQAEHARIKRGQDQLIKMAAAIQQP-KMWTLDRSTAPF-------------
SEQID NO:39 (197)   HLQTENARIKLQEQLLIAEATQNQ-VKRTLDRSFLLF----------------
SEQID NO:36 (156)   QLKQENKMLRYEELEGHSGQWIEKESIARFS MIFVSPRSGYVATLERV
SEQID NO:37 (167)   QLEEHEQLLLKDQLEASVEVSVI-VRKEL RVLSAFF-----------------
SEQID NO:3  (166)   LLQQEESLLVKDE LRESVEVAVEMVRKIL CMPSADE---------------
                        Z     Z                Z
```

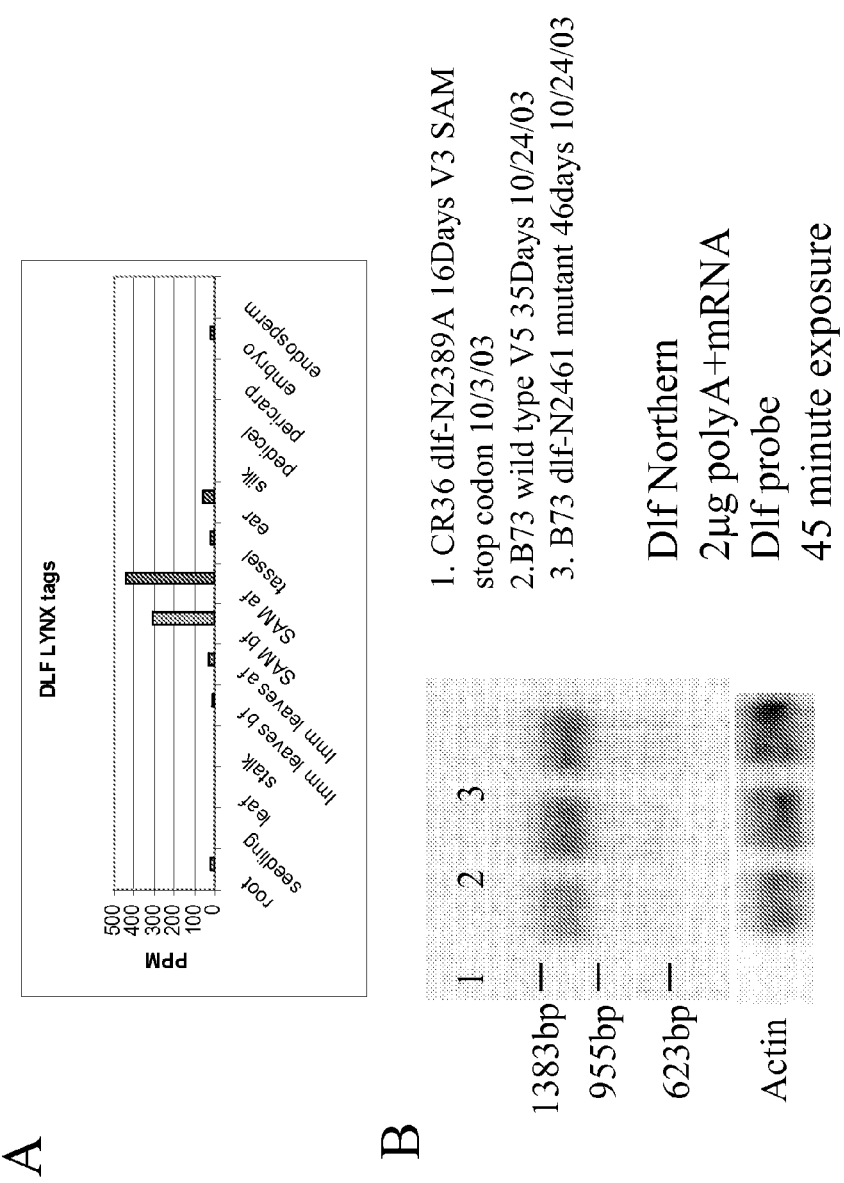
Figure 8 Electronic and experimental RNA analysis of the *DFL1* expression

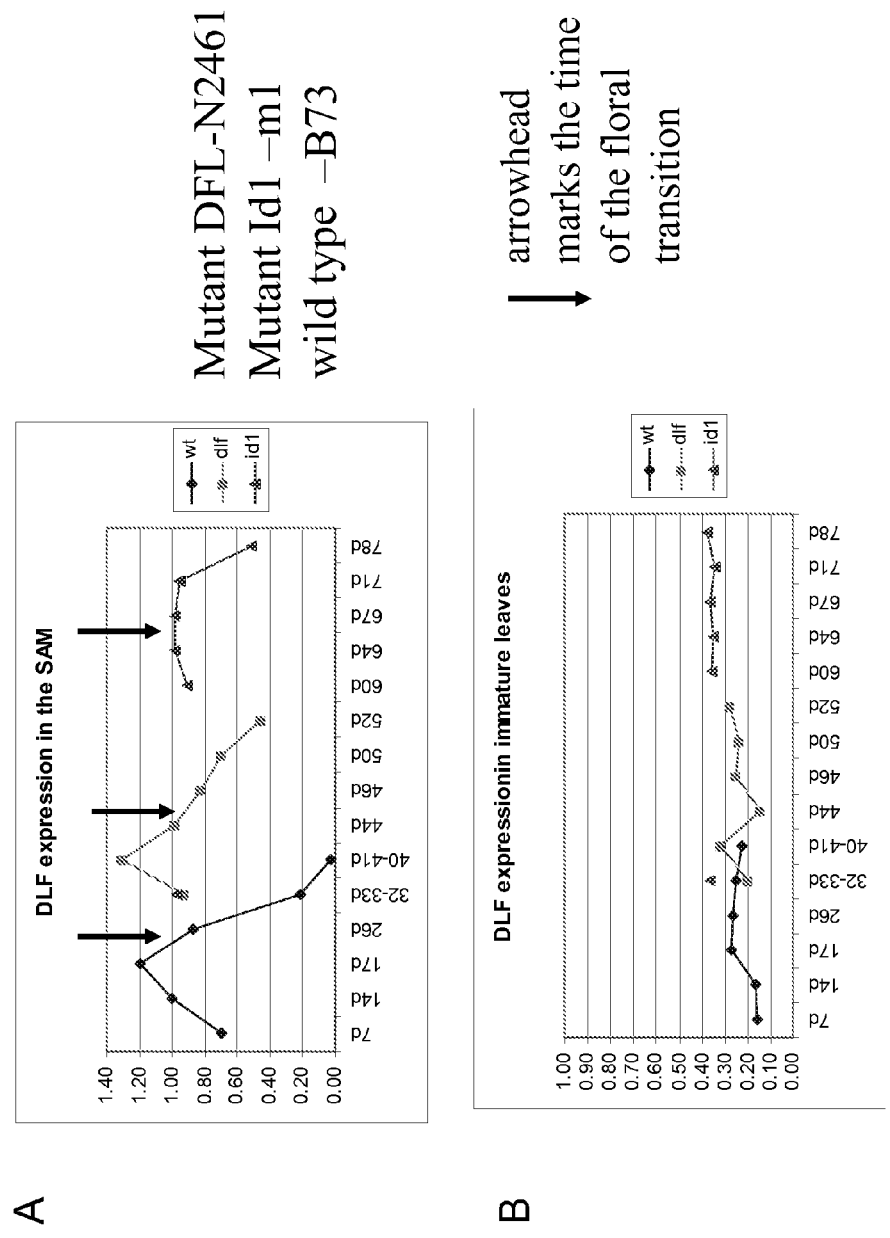
Figure 9. Temporal pattern of DFL1 expression during plant development (Quantitative RT-PCR, normalized over Ubiquitin)

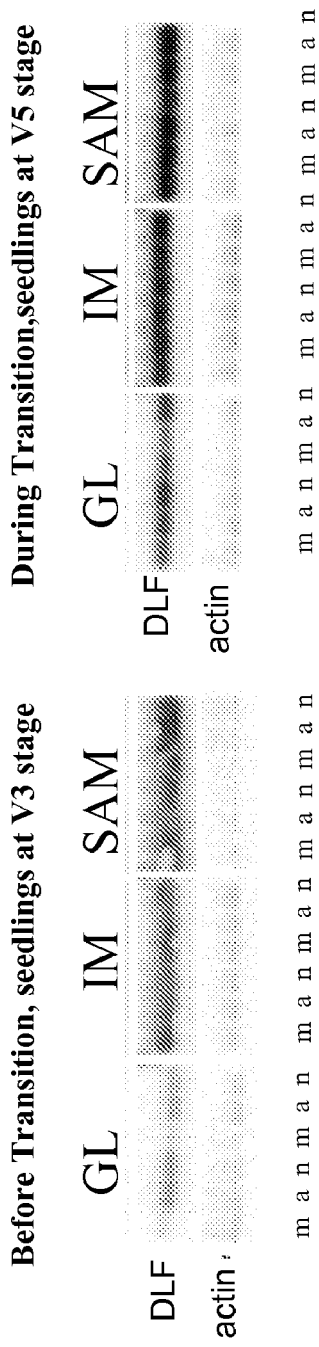
Figure 10. Photoperiod sensitivity of the *DFL1* transcription

DELAYED FLOWERING TIME GENE (DLF1) IN MAIZE AND USES THEREOF

CROSS REFERENCE

This utility application claims the benefit U.S. Provisional Application No. 60/760,839, filed Jan. 20, 2006, which is incorporated herein by reference.

BACKGROUND OF THE INVENTION

Flowering determines maturity, which is an economically important agronomic trait. Genes that control flowering time are essential for manipulation of maturity and optimization of yield. This invention describes cloning and characterization of the maize DLF1 gene (delayed flowering1) which controls the transition from vegetative to reproductive development (*Zea mays*).

The DLF1 gene is used for the manipulation of flowering time in plants, specifically monocots. Over-expression of this gene leads to early flowering, which is useful for seed yield in crops such as corn, rice, and wheat. The use of conditional, or inducible promoters allows one to control the timing of flower formation, to delay flowering when vegetative growth is advantageous, or accelerate flowering in breeding where reduced generation time is desired.

The DLF1 gene provides opportunities for adaptation of germplasm to different climatic zones. Developing early-flowering inbred lines will facilitate the movement of elite germplasm across maturity zones. This may be achieved by the over expression of the DLF1 gene.

SUMMARY OF THE INVENTION

The transition from vegetative to reproductive development is a critical point of plant development, ensuring the reproductive success of the species. Relatively few genes regulating this important agronomic trait have been identified for monocots. The sole maize flowering time gene cloned has been indeterminate1 (id1) which regulates a leaf-generated signal required for the transition to flowering. The subject of the present application is the cloning of the delayed flowering1 (DLF1) gene which also promotes the floral transition in maize. DLF1 mutants are late flowering, having an extended vegetative stage of growth and producing more leaves compared to wild type plants. A standard Mutator transposon tagging strategy was used to generate six new Mu-tagged dlf1 alleles. A modified PCR-based cloning method (Selected Amplification of Insertion Flanking Fragments, SAIFF) was used to isolate DLF1 gene-specific sequences. DLF1 encodes a protein with homology to bZIP transcription factors with a basic domain, leucine zippers and several putative phosphorylation sites. The dlf1 gene is most highly expressed in the shoot apical meristem. Transcript accumulates during vegetative growth, peaks prior to the floral transition and then diminishes in early reproductive growth. This pattern of expression of dlf1 is partially dependent on id1 functions, as dlf1 transcript does accumulate in id1-m1 mutants but is static. Homologous proteins were identified from the rice genome and the wheat EST databases. The monocot DLF proteins and *Arabidopsis* AtbZIP14 and AtbZIP27 define a distinct DLF-like bZIP subgroup. Loss-of-function mutations in the *Arabidopsis* AtbZIP14 gene (recently identified as the floral activator FD) cause a delay in flowering time, confirming that the DLF subgroup A of bZIP proteins share a role in regulating the floral transition in both monocots and dicots. 3-D protein modeling of a DLF1 missense mutation revealed a sensitive amino acid position that is predicted to affect DNA binding affinity.

Compositions and methods for improving crop plant reproductive development and yield by manipulation of DLF1 gene family in transgenic plants are provided The present invention provides polynucleotides, related polypeptides and conservatively modified variants of the DLF1 sequences. The polynucleotides and polypeptides of the invention include DLF1 genes, proteins and functional fragments or variants thereof.

The methods of the invention comprise introducing into a plant a polynucleotide and expressing the corresponding polypeptide within the plant. The sequences of the invention can be used to alter plant cell growth timing, leading to changes in plant reproductive development timing, thereby improving plant yield. The methods of the invention find use in improving plant reproductive synchronization, leading to increased yield.

Additionally provided are transformed plants, plant tissues, plant cells, seeds, and leaves. Such transformed plants, tissues, cells, seeds, and leaves comprise stably incorporated in their genomes at least one polynucleotide molecule of the invention.

One embodiment of the invention is an isolated polynucleotide selected from the group consisting of:
 (a) a polynucleotide having at least 80% sequence identity, as determined by the GAP algorithm under default parameters, to the full length sequence of a polynucleotide selected from the group consisting of SEQ ID NOS: 1 and 4; wherein the polynucleotide encodes a polypeptide that has reproductive tissue development regulator functions; and
 (b) a polynucleotide encoding a polypeptide consisting of SEQ ID NO: 2
 (c) a polynucleotide selected from the group consisting of SEQ ID NOS: 1 and 4; and
 (d) a polynucleotide which is complementary to the polynucleotide of (a), (b), or (c).

A second embodiment of the invention is recombinant expression cassette, comprising the polynucleotide of embodiment 1, wherein the polynucleotide is operably linked, in sense or anti-sense orientation, to a promoter.

A third embodiment is host cell comprising the expression cassette of embodiment 2.

A fourth embodiment is transgenic plant comprising the recombinant expression cassette of embodiment 2.

A fifth embodiment of the invention is the transgenic plant of embodiment 4, wherein said plant is a monocot.

A sixth embodiment of the invention is the transgenic plant of embodiment 4, wherein said plant is a dicot.

A seventh embodiment of the invention is the transgenic plant of embodiment 4, wherein said plant is selected from the group consisting of: maize, soybean, sunflower, sorghum, canola, wheat, alfalfa, cotton, rice, barley, millet, peanut and cocoa.

An eighth embodiment of the invention is the transgenic seed from the transgenic plant of embodiment 4.

Another embodiment of the invention is a method of increasing yield in plants, comprising:
 introducing into a plant cell a recombinant expression cassette comprising the polynucleotide of embodiment 1 operably linked to a promoter; and
 culturing the plant under plant cell growing conditions; wherein the plant architecture is improved.

An additional embodiment of the invention is the method of the preceding embodiment, wherein the plant cell is from a plant selected from the group consisting of: maize, soybean, sunflower, sorghum, canola, wheat, alfalfa, cotton, rice, barley, millet, peanut and cocoa.

Another embodiment of the invention is a method of increasing yield in a plant, comprising:
introducing into a plant cell a recombinant expression cassette comprising the polynucleotide of embodiment 1 operably linked to a promoter;
culturing the plant cell under plant cell growing conditions; and
regenerating a plant form said plant cell; wherein the plant architecture is improved.

One additional embodiment of the invention is a method of the preceding embodiment, wherein the plant is selected from the group consisting of: maize, soybean, sorghum, canola, wheat, alfalfa, cotton, rice, barley, millet, peanut, and cocoa.

BRIEF DESCRIPTION OF THE FIGURES

FIG. 1: The delayed flowering1 mutant phenotype is distinguished by an increase in leaf number (node number), increase in ear number and a delay in time to shed silk by about 10-14 days compared to wild type sib plants FIG. 2: PCR products paired with selective adaptor primers were separated on 1.5% agarose gel. A fragment segregating with the phenotype was identified. The nested PCR was repeated on all the individual plants (10 mu468 and 10 wild type). A perfect co-segregation was observed for a fragment 800nt.

FIG. 3: DLF1 gene, mRNA and protein structures

Genomic structure of the DLF1 gene was determined from sequencing of maize genomic DNA fragments cloned into BAC (bacterial artificial chromosomes) vectors. The 3486-nt unique sequence (SEQ ID NO: 1) (trimmed from retroelements on both sides) represents a complete copy of the DLF gene (A).

The 1.3-kb-cDNA (SEQ ID NO: 2) contains the 612-nt ORF and 550 nt 3'UTR (B). Alignment of the genomic DLF1 sequence and cDNA revealed one 80-nt intron (A). cDNA encoded putative protein of 204 amino acids (B). The DLF1 protein (SEQ ID NO: 3) contains a basic DNA biding domain, followed by four leucines (L) that formed a leucine zipper. Ten phosphorylation sites (P) are shown.

FIG. 4: Protein alignment of the DLF1 wild type protein, and reference EMS N2461 missense and N2389A nonsense mutants FIG. 5: Phylogenetic tree of plant bZIP proteins defining the DLF family FIG. 6: Phylogenetic tree of the group A of bZIP proteins FIG. 7: The amino acid alignment of proteins from the DLF1 clade FIG. 8: Expression pattern of the DLF1 gene in different tissues during plant development. To determine the tissue specific expression of the DLF1 gene the LYNX expression database were queried with a putative DLF1 cDNA. The 17-mer tag GATCCCATGTTTTTATT (SEQ ID NO: 4), positioned at 3'UTR (FIG. 3A) was found in the shoot apical meristem before and during the floral transition at 300-400 PPM (part per million).

FIG. 9: Quantitative RT-PCR was conducted on RNA, isolated from the shoot apical meristems and immature leaves at different stage of seedling development.

FIG. 10: Photosensitivity testing: RT-PCR was conducted on RNA, isolated from immature leaves, the top green leaves, and the shoot apical meristem at seedling of V3 stage (vegetative growth) and V7 stages (just after the floral transition, B73 inbred line). Tissues were collected during 48 hrs to cover twice the day-night cycle with 8 hrs intervals) under the long day condition (16-hrs day and 8-hrs night, temperature 25° C.). In the SAM and immature leaves the level of DLF1 transcripts remains the same around the clock. However, in green leaves the DLF1 transcription is lower in the morning hours and increased afternoon and during the night. This data indicate that DLF1 gene is a photoperiod sensitive gene and might be partly under control of the circadian cycle in the green leaves.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, BOTANY: PLANT BIOLOGY AND ITS RELATION TO HUMAN AFFAIRS, John Wiley (1982); CELL CULTURE AND SOMATIC CELL GENETICS OF PLANTS, vol. 1, Vasil, ed. (1984); Stanier, et al., THE MICROBIAL WORLD, $5^{th}$ ed., Prentice-Hall (1986); Dhringra and Sinclair, BASIC PLANT PATHOLOGY METHODS, CRC Press (1985); Maniatis, et al., MOLECULAR CLONING: A LABORATORY MANUAL (1982); DNA CLONING, vols. I and II, Glover, ed. (1985); OLIGONUCLEOTIDE SYNTHESIS, Gait, ed. (1984); NUCLEIC ACID HYBRIDIZATION, Hames and Higgins, eds. (1984); and the series METHODS IN ENZYMOLOGY, Colowick and Kaplan, eds, Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., DIAGNOSTIC MOLECULAR MICROBIOLOGY: PRINCIPLES AND APPLICATIONS, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60-90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W.H. Freeman and Co. (1984).

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (Yamao, et al., (1985) *Proc. Natl. Acad. Sci. USA* 82:2306-9), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids. Unless otherwise stated, the term "DLF1 nucleic acid" means a nucleic acid comprising a polynucleotide ("DLF1 polynucleotide") encoding a DLF1 polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, GUIDE TO MOLECULAR CLONING TECHNIQUES, from the series METHODS IN ENZYMOLOGY, vol. 152, Academic Press, Inc., San Diego, Calif. (1987); Sambrook, et al., MOLECULAR CLONING: A LABORATORY MANUAL, $2^{nd}$ ed., vols. 1-3 (1989); and CURRENT PROTOCOLS IN MOLECULAR BIOLOGY, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

As used herein, "yield" includes reference to bushels per acre of a grain crop at harvest, as adjusted for grain moisture (15% typically). Grain moisture is measured in the grain at harvest. The adjusted test weight of grain is determined to be the weight in pounds per bushel, adjusted for grain moisture level at harvest.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide," and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids, or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "DLF1 polypeptide" refers to one or more amino acid sequences. The term is also inclusive of fragments, variants, homologs, alleles or precursors (e.g., preproproteins or proproteins) thereof. A "DLF1 protein" comprises a DLF1 polypeptide. Unless otherwise stated, the term "DLF1 nucleic acid" means a nucleic acid comprising a polynucleotide ("DLF1 polynucleotide") encoding a DLF1 polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-84 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY-HYBRIDIZATION WITH NUCLEIC ACID PROBES, part 1, chapter 2, "Overview of principles of hybridization and the strategy of nucleic acid probe assays," Elsevier, New York (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Version 8 (available from Genetics Computer Group (GCG® programs (Accelrys, Inc., San Diego, Calif.).) The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65, and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The invention discloses DLF1 polynucleotides and polypeptides. The novel nucleotides and proteins of the invention have an expression pattern which indicates that they regulate reproductive tissue development and thus play an important role in plant development. The polynucleotides are expressed in various plant tissues. The polynucleotides and polypeptides thus provide an opportunity to manipulate plant development to alter seed and vegetative tissue development, timing or composition. This may be used to create a sterile plant, a seedless plant or a plant with altered endosperm composition.

Nucleic Acids

The present invention provides, inter alia, isolated nucleic acids of RNA, DNA, and analogs and/or chimeras thereof, comprising a DLF1 polynucleotide.

The present invention also includes polynucleotides optimized for expression in different organisms. For example, for expression of the polynucleotide in a maize plant, the sequence can be altered to account for specific codon preferences and to alter GC content as according to Murray, et al, supra. Maize codon usage for 28 genes from maize plants is listed in Table 4 of Murray, et al., supra.

The DLF1 nucleic acids of the present invention comprise isolated DLF1 polynucleotides which are inclusive of:
  (a) a polynucleotide encoding a DLF1 polypeptide and conservatively modified and polymorphic variants thereof;
  (b) a polynucleotide having at least 70% sequence identity with polynucleotides of (a) or (b);
  (c) complementary sequences of polynucleotides of (a) or (b).

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, PGEM, pSK+/−, pGEX, pSPORTI and II, pOPRSVI CAT, pOPI3 CAT, pXT1, pSG5, pPbac, pMbac, pMC1 neo, pOG44, pOG45, pFRTβGAL, pNEOβGAL, pRS403, pRS404, pRS405, pRS406, pRS413, pRS414, pRS415, pRS416, lambda MOSSIox, and lambda MOSElox. Optional vectors for the present invention, include but are not limited to, lambda ZAP II, and pGEX. For a description of various nucleic acids see, e.g., Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-9; the phosphodiester method of Brown, et al., (1979) *Meth. Enzymol.* 68:109-51; the diethylphosphoramidite method of Beaucage, et al., (1981) *Tetra. Letts.* 22(20): 1859-62; the solid phase phosphoramidite triester method described by Beaucage, et al., supra, e.g., using an automated synthesizer, e.g., as described in Needham-VanDevanter, et al., (1984) *Nucleic Acids Res.* 12:6159-68; and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 5<G>7 methyl GpppG RNA cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, supra, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group. See, Devereaux, et al., (1984) *Nucleic Acids Res.* 12:387-395); or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT publication No. 96/19256. See also, Zhang, et al., (1997) *Proc. Natl. Acad. Sci. USA* 94:4504-9; and Zhao, et al., (1998) *Nature Biotech* 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683, 439), the Nos promoter, the rubisco promoter, the GRP1-8 promoter, the 35S promoter from cauliflower mosaic virus (CaMV), as described in Odell, et al., (1985) *Nature* 313:810-2; rice actin (McElroy, et al., (1990) *Plant Cell* 163-171); ubiquitin (Christensen, et al., (1992) *Plant Mol. Biol.* 12:619-632 and Christensen, et al., (1992) *Plant Mol. Biol.* 18:675-89); pEMU (Last, et al., (1991) *Theor. Appl. Genet.* 81:581-8); MAS (Velten, et al., (1984) *EMBO J.* 3:2723-30); and maize H3 histone (Lepetit, et al., (1992) *Mol. Gen. Genet.* 231:276-85; and Atanassvoa, et al., (1992) *Plant Journal* 2(3):291-300); ALS promoter, as described in PCT Application No. WO 96/30530; and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50; and An, et al., (1989) *Plant Cell* 1:115-22); and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2, and 6, the Bronze-1 intron are known in the art. See generally, THE MAIZE HANDBOOK, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell,* 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119, and hereby incorporated by reference), or signal peptides which target proteins to the plastids such as that of rapeseed enoyl-Acp reductase (Verwaert, et al., (1994) *Plant Mol. Biol.* 26:189-202) are useful in the invention. The barley alpha amylase signal sequence fused to the DLF1 polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11, and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present invention.

Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., (1982) METHODS IN YEAST GENETICS, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th ed., 1992).

Appropriate vectors for expressing proteins of the present invention in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) *J. Embryol. Exp. Morphol.* 27:353-65).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in DNA CLONING: A PRACTICAL APPROACH, vol. II, Glover, ed., IRL Press, Arlington, Va., pp. 213-38 (1985)).

In addition, the gene for DLF1 placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert a DLF1 polynucleotide into a plant host, including biological and physical plant transformation protocols. See, e.g., Miki et al., (1993) "Procedure for Introducing Foreign DNA into Plants," in METHODS IN PLANT MOLECULAR BIOLOGY AND BIOTECHNOLOGY, Glick and Thompson, eds., CRC Press, Inc., Boca Raton, pp. 67-88. The methods chosen vary with the host plant, and include chemical transfection methods such as calcium phosphate, microorganism-mediated gene transfer such as *Agrobacterium* (Horsch, et al., (1985) *Science* 227:1229-31), electroporation, micro-injection, and biolistic bombardment.

Expression cassettes and vectors and in vitro culture methods for plant cell or tissue transformation and regeneration of plants are known and available. See, e.g., Gruber, et al., "Vectors for Plant Transformation," in METHODS IN PLANT MOLECULAR BIOLOGY AND BIOTECHNOLOGY, supra, pp. 89-119.

The isolated polynucleotides or polypeptides may be introduced into the plant by one or more techniques typically used for direct delivery into cells. Such protocols may vary depending on the type of organism, cell, plant or plant cell, i.e. monocot or dicot, targeted for gene modification. Suitable methods of transforming plant cells include microinjection (Crossway, et al., (1986) *Biotechniques* 4:320-334; and U.S. Pat. No. 6,300,543), electroporation (Riggs, et al., (1986) *Proc. Natl. Acad. Sci. USA* 83:5602-5606, direct gene transfer (Paszkowski, et al., (1984) *EMBO J.* 3:2717-2722), and ballistic particle acceleration (see, for example, Sanford et al., U.S. Pat. No. 4,945,050; WO 91/10725; and McCabe, et al., (1988) *Biotechnology* 6:923-926). Also see, Tomes, et al., Direct DNA Transfer into Intact Plant Cells Via Microprojectile Bombardment. pp. 197-213 in Plant Cell, Tissue and Organ Culture, Fundamental Methods. eds. O. L. Gamborg & G. C. Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839; and Gordon-Kamm, et al., (1990) *Plant Cell* 2:603-618 (maize); Hooydaas-Van Slogteren & Hooykaas, (1984) *Nature* (London) 311:763-764; Bytebier, et al., (1987) *Proc. Natl. Acad. Sci. USA* 84:5345-5349 (Liliaceae); De Wet, et al., (1985) In The Experimental Manipulation of Ovule Tissues, ed. G. P. Chapman, et al., pp. 197-209. Longman, N.Y. (pollen); Kaeppler, et al., (1990) *Plant Cell Reports* 9:415-418; and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255; and Christou & Ford (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer & Finer (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185); all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit Rev. Plant Sci.* 10:1. Descriptions of the *Agrobacterium* vector systems and methods for *Agrobacterium*-mediated gene transfer are provided in Gruber, et al., supra; Miki, et al., supra; and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658, 082; U.S. patent application Ser. No. 913,914, filed Oct. 1, 1986, as referenced in U.S. Pat. No. 5,262,306, issued Nov. 16, 1993; and Simpson, et al., (1986) Plant Mol. Biol. 6:403-15 (also referenced in the '306 patent); all incorporated by reference in their entirety.

Once constructed, these plasmids can be placed into A. rhizogenes or A. tumefaciens and these vectors used to transform cells of plant species, which are ordinarily susceptible to Fusarium or Alternaria infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either A. tumefaciens or A. rhizogenes will depend on the plant being transformed thereby. In general A. tumefaciens is the preferred organism for transformation. Most dicotyledonous plants, some gymnosperms, and a few monocotyledonous plants (e.g., certain members of the Liliales and Arales) are susceptible to infection with A. tumefaciens. A. rhizogenes also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using Agrobacterium. European Application No. 672 752 A1 discloses a method for transforming monocots with Agrobacterium using the scutellum of immature embryos. Ishida, et al., discuss a method for transforming maize by exposing immature embryos to A. tumefaciens (Nature Biotechnology 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with A. rhizogenes or A. tumefaciens, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra; and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206; and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731; and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161; and Draper, et al., (1982) *Plant Cell Physiol.* 23:451.

Electroporation of protoplasts and whole cells and tissues has also been described. See, e.g., Donn, et al., (1990) Abstracts of the VIIth Int'l. *Congress on Plant Cell and Tissue Culture IAPTC*, A2-38, p. 53; D'Halluin, et al., (1992) *Plant Cell* 4:1495-505; and Spencer, et al., (1994) *Plant Mol. Biol.* 24:51-61.

Increasing the Activity and/or Level of a DLF1 Polypeptide

Methods are provided to increase the activity and/or level of the DLF1 polypeptide of the invention. An increase in the level and/or activity of the DLF1 polypeptide of the invention can be achieved by providing to the plant a DLF1 polypeptide. The DLF1 polypeptide can be provided by introducing the amino acid sequence encoding the DLF1 polypeptide into the plant, introducing into the plant a nucleotide sequence encoding a DLF1 polypeptide or alternatively by modifying a genomic locus encoding the DLF1 polypeptide of the invention.

As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having reproductive tissue development regulator activity. It is also recognized that the methods of the invention may employ a polynucleotide that is not capable of directing, in the transformed plant, the expression of a protein or an RNA. Thus, the level and/or activity of a DLF1 polypeptide may be increased by altering the gene encoding the DLF1 polypeptide or its promoter. See, e.g., Kmiec, U.S. Pat. No. 5,565,350; Zarling, et al., PCT/US93/03868. Therefore mutagenized plants that carry mutations in DLF1 genes, where the mutations increase expression of the DLF1 gene or increase the reproductive tissue development regulator activity of the encoded DLF1 polypeptide are provided.

Reducing the Activity and/or Level of a DLF1 Polypeptide

Methods are provided to reduce or eliminate the activity of a DLF1 polypeptide of the invention by transforming a plant cell with an expression cassette that expresses a polynucleotide that inhibits the expression of the DLF1 polypeptide. The polynucleotide may inhibit the expression of the DLF1 polypeptide directly, by preventing translation of the DLF1 messenger RNA, or indirectly, by encoding a polypeptide that inhibits the transcription or translation of a DLF1 gene encoding a DLF1 polypeptide. Methods for inhibiting or eliminating the expression of a gene in a plant are well known in the art, and any such method may be used in the present invention to inhibit the expression of a DLF1 polypeptide.

In accordance with the present invention, the expression of a DLF1 polypeptide is inhibited if the protein level of the DLF1 polypeptide is less than 70% of the protein level of the same DLF1 polypeptide in a plant that has not been genetically modified or mutagenized to inhibit the expression of that DLF1 polypeptide. In particular embodiments of the invention, the protein level of the DLF1 polypeptide in a modified plant according to the invention is less than 60%, less than 50%, less than 40%, less than 30%, less than 20%, less than 10%, less than 5%, or less than 2% of the protein level of the same DLF1 polypeptide in a plant that is not a mutant or that has not been genetically modified to inhibit the expression of that DLF1 polypeptide. The expression level of the DLF1 polypeptide may be measured directly, for example, by assaying for the level of DLF1 polypeptide expressed in the plant cell or plant, or indirectly, for example, by measuring the reproductive tissue development regulator activity of the DLF1 polypeptide in the plant cell or plant, or by measuring the reproductive tissue development in the plant. Methods for performing such assays are described elsewhere herein.

In other embodiments of the invention, the activity of the DLF1 polypeptides is reduced or eliminated by transforming a plant cell with an expression cassette comprising a polynucleotide encoding a polypeptide that inhibits the activity of a DLF1 polypeptide. The reproductive tissue development regulator activity of a DLF1 polypeptide is inhibited according to the present invention if the reproductive tissue development regulator activity of the DLF1 polypeptide is less than 70% of the reproductive tissue development regulator activity of the same DLF1 polypeptide in a plant that has not been modified to inhibit the reproductive tissue development regulator activity of that DLF1 polypeptide. In particular embodiments of the invention, the reproductive tissue development regulator activity of the DLF1 polypeptide in a modified plant according to the invention is less than 60%, less than 50%, less than 40%, less than 30%, less than 20%, less than 10%, or less than 5% of the reproductive tissue development regulator activity of the same DLF1 polypeptide in a plant that that has not been modified to inhibit the expression of that DLF1 polypeptide. The reproductive tissue development regulator activity of a DLF1 polypeptide is "eliminated" according to the invention when it is not detectable by the assay methods described elsewhere herein. Methods of determining the reproductive tissue development regulator activity of a DLF1 polypeptide are described elsewhere herein.

In other embodiments, the activity of a DLF1 polypeptide may be reduced or eliminated by disrupting the gene encoding the DLF1 polypeptide. The invention encompasses mutagenized plants that carry mutations in DLF1 genes, where the mutations reduce expression of the DLF1 gene or inhibit the reproductive tissue development regulator activity of the encoded DLF1 polypeptide.

Thus, many methods may be used to reduce or eliminate the activity of a DLF1 polypeptide. In addition, more than one method may be used to reduce the activity of a single DLF1 polypeptide. Non-limiting examples of methods of reducing or eliminating the expression of DLF1 polypeptides are given below.

1. Polynucleotide-Based Methods:

In some embodiments of the present invention, a plant is transformed with an expression cassette that is capable of expressing a polynucleotide that inhibits the expression of a DLF1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one DLF1 polypeptide is an expression cassette capable of producing an RNA molecule that inhibits the transcription and/or translation of at least one DLF1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a DLF1 polypeptide are given below.

i. Sense Suppression/Cosuppression

In some embodiments of the invention, inhibition of the expression of a DLF1 polypeptide may be obtained by sense suppression or cosuppression. For cosuppression, an expression cassette is designed to express an RNA molecule corresponding to all or part of a messenger RNA encoding a DLF1 polypeptide in the "sense" orientation. Over expression of the RNA molecule can result in reduced expression of the native gene. Accordingly, multiple plant lines transformed with the cosuppression expression cassette are screened to identify those that show the greatest inhibition of DLF1 polypeptide expression.

The polynucleotide used for cosuppression may correspond to all or part of the sequence encoding the DLF1 polypeptide, all or part of the 5' and/or 3' untranslated region of a DLF1 polypeptide transcript, or all or part of both the coding sequence and the untranslated regions of a transcript encoding a DLF1 polypeptide. In some embodiments where the polynucleotide comprises all or part of the coding region for the DLF1 polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dt region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323; herein incorporated by reference.

ii. Antisense Suppression

In some embodiments of the invention, inhibition of the expression of the DLF1 polypeptide may be obtained by antisense suppression. For antisense suppression, the expression cassette is designed to express an RNA molecule complementary to all or part of a messenger RNA encoding the DLF1 polypeptide. Over expression of the antisense RNA molecule can result in reduced expression of the native gene. Accordingly, multiple plant lines transformed with the antisense suppression expression cassette are screened to identify those that show the greatest inhibition of DLF1 polypeptide expression.

The polynucleotide for use in antisense suppression may correspond to all or part of the complement of the sequence encoding the DLF1 polypeptide, all or part of the complement of the 5' and/or 3' untranslated region of the DLF1 transcript, or all or part of the complement of both the coding sequence and the untranslated regions of a transcript encoding the DLF1 polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550, or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dt region in the expression cassette at a position 3' to the antisense sequence and 5' of the polyadenylation signal. See, U.S. Patent Publication No. 20020048814, herein incorporated by reference.

iii. Double-Stranded RNA Interference

In some embodiments of the invention, inhibition of the expression of a DLF1 polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of DLF1 polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

iv. Hairpin RNA Interference and Intron-Containing Hairpin RNA Interference

In some embodiments of the invention, inhibition of the expression of one or a DLF1 polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk, et al., (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk, et al., (2002) *Plant Physiol.* 129:1723-1731; Waterhouse and Helliwell (2003) *Nat. Rev. Genet.* 4:29-38; Pandolfini, et al., *BMC Biotechnology* 3:7, and U.S. Patent Publication No. 20030175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the DLF1 polypeptide). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

vi. Ribozymes

In some embodiments, the polynucleotide expressed by the expression cassette of the invention is catalytic RNA or has ribozyme activity specific for the messenger RNA of the DLF1 polypeptide. Thus, the polynucleotide causes the degradation of the endogenous messenger RNA, resulting in reduced expression of the DLF1 polypeptide. This method is described, for example, in U.S. Pat. No. 4,987,071, herein incorporated by reference.

vii. Small Interfering RNA or Micro RNA

In some embodiments of the invention, inhibition of the expression of a DLF1 polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of DLF1 expression, the 22-nucleotide sequence is selected from a DLF1 transcript sequence and contains 22 nucleotides of said DLF1 sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a DLF1 polypeptide, resulting in reduced expression of the gene. In particular embodiments, the zinc finger protein binds to a regulatory region of a DLF1 gene. In other embodiments, the zinc finger protein binds to a messenger RNA encoding a DLF1 polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

3. Polypeptide-Based Inhibition of Protein Activity

In some embodiments of the invention, the polynucleotide encodes an antibody that binds to at least one DLF1 polypeptide, and reduces the reproductive tissue development regulator activity of the DLF1 polypeptide. In another embodiment, the binding of the antibody results in increased turnover of the antibody-DLF1 complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

4. Gene Disruption

In some embodiments of the present invention, the activity of a DLF1 polypeptide is reduced or eliminated by disrupting the gene encoding the DLF1 polypeptide. The gene encoding the DLF1 polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced reproductive tissue development regulator activity.

i. Transposon Tagging

In one embodiment of the invention, transposon tagging is used to reduce or eliminate the DLF1 activity of one or more DLF1 polypeptide. Transposon tagging comprises inserting a transposon within an endogenous DLF1 gene to reduce or eliminate expression of the DLF1 polypeptide. "DLF1 gene" is intended to mean the gene that encodes a DLF1 polypeptide according to the invention.

In this embodiment, the expression of one or more DLF1 polypeptide is reduced or eliminated by inserting a transposon within a regulatory region or coding region of the gene encoding the DLF1 polypeptide. A transposon that is within an exon, intron, 5' or 3' untranslated sequence, a promoter, or any other regulatory sequence of a DLF1 gene may be used to reduce or eliminate the expression and/or activity of the encoded DLF1 polypeptide.

Methods for the transposon tagging of specific genes in plants are well known in the art. See, for example, Maes, et al., (1999) *Trends Plant Sci.* 4:90-96; Dharmapuri and Sonti (1999) *FEMS Microbiol. Lett.* 179:53-59; Meissner, et al., (2000) *Plant J.* 22:265-274; Phogat, et al., (2000) *J. Biosci.* 25:57-63; Walbot (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540; and U.S. Pat. No. 5,962,764; each of which is herein incorporated by reference.

ii. Mutant Plants with Reduced Activity

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874; and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (reproductive tissue development regulator activity) of the encoded protein are well known in the art. Insertional mutations in gene exons usually result in null-mutants. Mutations in conserved residues are particularly effective in inhibiting the reproductive tissue development regulator activity of the encoded protein. Conserved residues of plant DLF1 polypeptides suitable for mutagenesis with the goal to eliminate reproductive tissue development regulator activity have been described. Such mutants can be isolated according to well-known procedures, and mutations in different DLF1 loci can be stacked by genetic crossing. See, for example, Gruis, et al., (2002) *Plant Cell* 14:2863-2882.

In another embodiment of this invention, dominant mutants can be used to trigger RNA silencing due to gene inversion and recombination of a duplicated gene locus. See, for example, Kusaba, et al., (2003) *Plant Cell* 15:1455-1467.

The invention encompasses additional methods for reducing or eliminating the activity of one or more DLF1 polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

iii. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development, or radial expansion.

Methods for modulating root development in a plant are provided. The methods comprise modulating the level and/or activity of the DLF1 polypeptide in the plant. In one method, a DLF1 sequence of the invention is provided to the plant. In another method, the DLF1 nucleotide sequence is provided by introducing into the plant a polynucleotide comprising a DLF1 nucleotide sequence of the invention, expressing the DLF1 sequence, and thereby modifying root development. In still other methods, the DLF1 nucleotide construct introduced into the plant is stably incorporated into the genome of the plant.

In other methods, root development is modulated by altering the level or activity of the DLF1 polypeptide in the plant. A decrease in DLF1 activity can result in at least one or more of the following alterations to root development, including, but not limited to, larger root meristems, increased in root growth, enhanced radial expansion, an enhanced vasculature system, increased root branching, more adventitious roots, and/or an increase in fresh root weight when compared to a control plant.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, U.S. Application No. 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the DLF1 polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by decreasing the level and/or activity of the DLF1 polypeptide also finds use in promoting in vitro propagation of explants.

Furthermore, higher root biomass production due to an decreased level and/or activity of DLF1 activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present invention further provides plants having modulated root development when compared to the root development of a control plant. In some embodiments, the plant of the invention has an increased level/activity of the DLF1 polypeptide of the invention and has enhanced root growth and/or root biomass. In other embodiments, such plants have stably incorporated into their genome a nucleic acid molecule comprising a DLF1 nucleotide sequence of the invention operably linked to a promoter that drives expression in the plant cell.

iv. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length, and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and U.S. Application No. 2003/0074698, each of which is herein incorporated by reference.

The method for modulating shoot and/or leaf development in a plant comprises modulating the activity and/or level of a DLF1 polypeptide of the invention. In one embodiment, a DLF1 sequence of the invention is provided. In other embodiments, the DLF1 nucleotide sequence can be provided by introducing into the plant a polynucleotide comprising a DLF1 nucleotide sequence of the invention, expressing the DLF1 sequence, and thereby modifying shoot and/or leaf development. In other embodiments, the DLF1 nucleotide construct introduced into the plant is stably incorporated into the genome of the plant.

In specific embodiments, shoot or leaf development is modulated by increasing the level and/or activity of the DLF1 polypeptide in the plant. An increase in DLF1 activity can result in at least one or more of the following alterations in shoot and/or leaf development, including, but not limited to, reduced leaf number, reduced leaf surface, reduced vascular, shorter internodes and stunted growth, and retarded leaf senescence, when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters, and leaf-preferred promoters. Exemplary promoters have been disclosed elsewhere herein.

Increasing DLF1 activity and/or level in a plant results in shorter internodes and stunted growth. Thus, the methods of the invention find use in producing dwarf plants. In addition, as discussed above, modulation DLF1 activity in the plant modulates both root and shoot growth. Thus, the present invention further provides methods for altering the root/shoot ratio. Shoot or leaf development can further be modulated by decreasing the level and/or activity of the DLF1 polypeptide in the plant.

Accordingly, the present invention further provides plants having modulated shoot and/or leaf development when compared to a control plant. In some embodiments, the plant of the invention has an increased level/activity of the DLF1 polypeptide of the invention. In other embodiments, the plant of the invention has a decreased level/activity of the DLF1 polypeptide of the invention.

v Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the DLF1 polypeptide has not been modulated. "Modulating floral development" further includes any alteration in the timing of the development of a plant's reproductive tissue (i.e., a delayed or a accelerated timing of floral development) when compared to a control plant in which the activity or level of the DLF1 polypeptide has not been modulated. Macroscopic alterations may include changes in size, shape, number, or location of reproductive organs, the developmental time period that these structures form, or the ability to maintain or proceed through the flowering process in times of environmental stress. Microscopic alterations may include changes to the types or shapes of cells that make up the reproductive organs.

The method for modulating floral development in a plant comprises modulating DLF1 activity in a plant. In one method, a DLF1 sequence of the invention is provided. A DLF1 nucleotide sequence can be provided by introducing into the plant a polynucleotide comprising a DLF1 nucleotide sequence of the invention, expressing the DLF1 sequence, and thereby modifying floral development. In other embodiments, the DLF1 nucleotide construct introduced into the plant is stably incorporated into the genome of the plant.

In specific methods, floral development is modulated by increasing the level or activity of the DLF1 polypeptide in the plant. An increase in DLF1 activity can result in at least one or more of the following alterations in floral development, including, but not limited to, retarded flowering, reduced number of flowers, partial male sterility, and reduced seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters, and inflorescence-preferred promoters.

In other methods, floral development is modulated by decreasing the level and/or activity of the DLF1 sequence of the invention. Such methods can comprise introducing a DLF1 nucleotide sequence into the plant and decreasing the activity of the DLF1 polypeptide. In other methods, the DLF1 nucleotide construct introduced into the plant is stably incorporated into the genome of the plant. Decreasing expression of the DLF1 sequence of the invention can modulate floral development during periods of stress. Such methods are described elsewhere herein. Accordingly, the present invention further provides plants having modulated floral development when compared to the floral development of a control plant. Compositions include plants having a decreased level/activity of the DLF1 polypeptide of the invention and having an altered floral development. Compositions also include plants having a decreased level/activity of the DLF1 polypeptide of the invention wherein the plant maintains or proceeds through the flowering process in times of stress.

Methods are also provided for the use of the DLF1 sequences of the invention to increase seed size and/or weight. The method comprises increasing the activity of the DLF1 sequences in a plant or plant part, such as the seed. An increase in seed size and/or weight comprises an increased size or weight of the seed and/or an increase in the size or weight of one or more seed part including, for example, the embryo, endosperm, seed coat, aleurone, or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters, and endosperm-preferred promoters.

The method for decreasing seed size and/or seed weight in a plant comprises increasing DLF1 activity in the plant. In one embodiment, the DLF1 nucleotide sequence can be provided by introducing into the plant a polynucleotide comprising a DLF1 nucleotide sequence of the invention, expressing the DLF1 sequence, and thereby decreasing seed weight and/or size. In other embodiments, the DLF1 nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present invention further provides plants having an increased seed weight and/or seed size when compared to a control plant. In other embodiments, plants having an increased vigor and plant yield are also provided. In some embodiments, the plant of the invention has a decreased level/activity of the DLF1 polypeptide of the invention and has an increased seed weight and/or seed size. In other embodiments, such plants have stably incorporated into their genome a nucleic acid molecule comprising a DLF1 nucleotide sequence of the invention operably linked to a promoter that drives expression in the plant cell.

vi. Method of Use for DLF1 Promoter Polynucleotides

The polynucleotides comprising the DLF1 promoters disclosed in the present invention, as well as variants and fragments thereof, are useful in the genetic manipulation of any host cell, preferably plant cell, when assembled with a DNA construct such that the promoter sequence is operably linked to a nucleotide sequence comprising a polynucleotide of interest. In this manner, the DLF1 promoter polynucleotides of the invention are provided in expression cassettes along with a polynucleotide sequence of interest for expression in the host cell of interest. The DLF1 promoter sequences of the invention are expressed in a variety of tissues and thus the promoter sequences can find use in regulating the temporal and/or the spatial expression of polynucleotides of interest.

Synthetic hybrid promoter regions are known in the art. Such regions comprise upstream promoter elements of one polynucleotide operably linked to the promoter element of another polynucleotide. In an embodiment of the invention, heterologous sequence expression is controlled by a synthetic hybrid promoter comprising the DLF1 promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton, et al., (1998) *Curr. Opin. Plant Biol.* 1:311-315. Alternatively, a synthetic DLF1 promoter sequence may comprise duplications of the upstream promoter elements found within the DLF1 promoter sequences.

It is recognized that the promoter sequence of the invention may be used with its native DLF1 coding sequences. A DNA construct comprising the DLF1 promoter operably linked with its native DLF1 gene may be used to transform any plant of interest to bring about a desired phenotypic change, such as modulating cell number, modulating root, shoot, leaf, floral, and embryo development, stress tolerance, and any other phenotype described elsewhere herein.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

In certain embodiments the nucleic acid sequences of the present invention can be used in combination ("stacked") with other polynucleotide sequences of interest in order to create plants with a desired phenotype. The combinations generated can include multiple copies of any one or more of the polynucleotides of interest. The polynucleotides of the present invention may be stacked with any gene or combination of genes to produce plants with a variety of desired trait combinations, including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson, et al., (1987) *Eur. J. Biochem.* 165:99-106; and WO 98/20122); and high methionine proteins (Pedersen, et al., (1986) *J. Biol. Chem.* 261:6279; Kirihara, et al., (1988) *Gene* 71:359; and Musumura, et al., (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see U.S. Pat. No. 5,583,210), stalk strength, flowering time, or transformation technology traits such as cell cycle regulation or gene targeting (e.g., WO 99/61619; WO 00/17364; WO 99/25821), the disclosures of which are herein incorporated by reference.

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane H$^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115: 1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359; both of which are herein incorporated by reference); and rice (Musumura, et al., (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser, et al., (1986) *Gene* 48:109); and the like.

Genes encoding disease resistance traits include detoxification genes, such as against fumonosin (U.S. Pat. No. 5,792, 931); avirulence (avr) and disease resistance (R) genes (Jones, et al., (1994) *Science* 266:789; Martin, et al., (1993) *Science* 262:1432; and Mindrinos, et al., (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see, Schubert, et al., (1988) *J. Bacteriol.* 170:5837-5847) facilitate expression of polyhydroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

This invention can be better understood by reference to the following non-limiting examples. It will be appreciated by those skilled in the art that other embodiments of the invention may be practiced without departing from the spirit and the scope of the invention as herein disclosed and claimed.

Example 1

Transformation and Regeneration of Transgenic Plants

Immature maize embryos from greenhouse donor plants are bombarded with a plasmid containing a polynucleotide comprising the sequence set forth in SEQ ID NO: 1 or 4 operably linked to a promoter that, when expressed, regulates reproductive tissue development, where the plasmid further contains the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector is made comprising a polynucleotide sequence of SEQ ID NO: 1 or 4 operably linked to a promoter that, when expressed, regulates reproductive tissue development. This plasmid DNA plus plasmid DNA containing a PAT selectable marker is precipitated onto 1.1 µm (average diameter) tungsten pellets using a CaCl$_2$ precipitation procedure as follows: 100 µl prepared tungsten particles in water; 10 µl (1

μg) DNA in Tris EDTA buffer (1 μg total DNA); 100 μl 2.5 M CaCl$_2$; and 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for reproductive tissue development changes.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 2

*Agrobacterium*-Mediated Transformation

For *Agrobacterium*-mediated transformation of maize with a construct comprising a polynucleotide sequence of the invention such as SEQ ID NO: 1 or 4 capable of regulating reproductive tissue development operably linked to a promoter, the method of Zhao is employed (U.S. Pat. No. 5,981,840, and International Patent Publication No. WO 98/32326; the contents of which are hereby incorporated by reference). Briefly, immature embryos are isolated from maize and the embryos contacted with a suspension of *Agrobacterium*, where the bacteria are capable of transferring the construct comprising a polynucleotide sequence of the invention such as SEQ ID NO: 1 or 4 capable of regulating reproductive tissue development operably linked to a promoter, to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 3

Soybean Embryo Transformation

Soybean embryos are bombarded with a plasmid containing the construct comprising a polynucleotide sequence of the invention such as SEQ ID NO: 1 or 4 capable of regulating reproductive tissue development operably linked to a promoter, as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188), and the 3' region of the nopaline synthase gene from the T-DNA of the Ti plasmid of *Agrobacterium tumefaciens*. The expression cassette comprising a polynucleotide sequence of the invention such as SEQ ID NO: 1 or 4 operably linked to a promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl $CaCl_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post-bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 4

Mutant Phenotype, Mu-Tagging, Genetic Crosses, Segregation Analysis

The delayed flowering1 mutant phenotype is distinguished by an increase in leaf number (node number), increase in ear number and a delay in time to shed and silk by about 10-14 days compared to wild type sib plants (FIG. 1). The mutant phenotype suggests the normal function of the DLF1 protein is to promote flowering or the floral transition and when nonfunctional, results in late flowering. Outcrossing mutant plants to any inbred produced 100% wild type (normal) F1 progeny indicating the dlf1 mutation was recessive. Self-pollination of any F1 produced F2 families segregating 75% wild type and 25% dlf1 mutant plants proving the dlf1 was a single Mendelian recessive mutation. Directed Mu-tagging was set-up in PW 1996 using homozygous dlf1-ref mutant plants as the pollen parent and crossing to various active Mutator female lines. All of the resulting F1 progeny were heterozygous and most had a wild type phenotype. At a very low frequency ($10^{-4}$ to $10^{-5}$), F1 progeny produced a mutant dlf1-type late flowering phenotype when a Mu transposon inserted into the dlf1 locus in the active Mu parent. Such mutant F1 plants were heteroallelic with the dlf1-ref allele and a new, putatively Mu-tagged dlf1-mu allele. Such plants stood out as being taller, with more leaves (nodes) and flowered later than all the other F1 plants. Six mu-tagged alleles were recovered mu469, mu468, mu466, mu464, mu461, mu453, and one mu710 was found in an active Mutator population. These mu-tagged mutants were used for cloning.

Example 5

Cloning of DLF by Mu-Tagging: Isolation of Mu-Adjacent Fragment that Co-Segregates with the DLF Phenotype by SAIFF (Selected Amplification of Insertion Flanking Fragments)

Genomic DNA (~0.3 μg) from Mu-tagged mutants (allele mu468) and wild type plants (10 each) were digested with MseI in 1×RL buffer (10 mM Tris.HCl, pH 7.5, 10 mM MgoAc, 50 mM KoAc, 5 mM DTT) at 37° C. for 3 hr in a final volume of 25 ul. Following denaturation at 65° C. for 20 min, 5 ul ligation mix (0.3 ul 100 mM rATP, 0.5 ul 10×RL buffer, 1 ul 40 uM adaptor, 1 ul T4 ligase (3 U/ul, Promega), and 2.2 ul of water) were added to each digestion reaction. The MseI adaptor is a mixture of 5'-TACTCAGGACTCATCGACCGT (SEQ ID NO: 5) and 5'-GTGAACGGTCGATGAGTCCT-GAG (SEQ ID NO: 6). After overnight incubation at 4° C., the ligation reactions were purified with the Qiagen PCR Purification kit to remove the excess adaptor.

The Mu-flanking fragments were amplified with Mu TIR primer MuExt22D (5'-CCAACGCCAWSGCCTCYATTTC (SEQ ID NO: 7)) and MseI adaptor primer MseExt18 (5'-GTGAACGGTCGATGAGTC) (SEQ ID NO: 8) with Qiagen's HotStartTaq DNA polymerase. A 2-ul aliquot of the purified ligation reaction was used in 10-ul PCR reaction, with a final of 5% DMSO. The cycling conditions were 95° C. 15 min, [94° C. 30 sec, 55° C. 30 sec, 72° C. 2 min 30 sec]×20 cycles, 72° C. 7 min. Dilute the PCR reaction 1:10 by adding 90 ul of water. Take equal volume from each reaction and make the Mu+ and Mu− pools (10 plants/pool).

Mu-flanking fragments from both Mu+ and Mu− pools were amplified with nested Mu TIR primer MuInt19 (5'-CCTCYATTTCGTCGAATC) (SEQ ID NO: 9) and +2 selective adaptor primers with Takara's Ex Taq DNA polymerase. There're a total of 16+2 selective primers

| | | |
|---|---|---|
| (MseIntAAA: | CGATGAGTCCTGAGTAAAA, | (SEQ ID NO: 10) |
| MseIntAAC: | CGATGAGTCCTGAGTAAAC, | (SEQ ID NO: 11) |
| MseIntAAG: | CGATGAGTCCTGAGTAAAG, | (SEQ ID NO: 12) |
| MseIntAAT: | CGATGAGTCCTGAGTAAAT, | (SEQ ID NO: 13) |
| MseIntACA: | CGATGAGTCCTGAGTAACA, | (SEQ ID NO: 14) |
| MseIntACC: | GATGAGTCCTGAGTAACC, | (SEQ ID NO: 15) |
| MseIntACG: | GATGAGTCCTGAGTAACG, | (SEQ ID NO: 16) |
| MseIntACT: | GATGAGTCCTGAGTAACT, | (SEQ ID NO: 17) |

-continued

```
MseIntAGA:  CGATGAGTCCTGAGTAAGA,   (SEQ ID NO: 18)

MseIntAGC:  GATGAGTCCTGAGTAAGC,    (SEQ ID NO: 19)

MseIntAGG:  GATGAGTCCTGAGTAAGG,    (SEQ ID NO: 20)

MseIntAGT:  CGATGAGTCCTGAGTAAGT,   (SEQ ID NO: 21)

MseIntATA:  CGATGAGTCCTGAGTAATA,   (SEQ ID NO: 22)

MseIntATC:  GATGAGTCCTGAGTAATC,    (SEQ ID NO: 23)

MseIntATG:  GATGAGTCCTGAGTAATG,    (SEQ ID NO: 24)

MseIntATT:  CGATGAGTCCTGAGTAATT.   (SEQ ID NO :25)
```

A 1-ul aliquot of the pooled PCR reaction was used in 10-ul PCR reaction, with a final of 5% DMSO. The touchdown cycling conditions were 95° C. 2 min, [94° C. 30 sec, 65° C.-0.8° C./cycle 30 sec, 72° C. 2 min 30 sec]×11 cycles, [94° C. 30 sec, 56° C. 30 sec, 72° C. 2 min 30 sec]×24 cycles, 72° C. 7 min.

The PCR products of MuInt19 paired with 16+2 selective adaptor primers were separated on 1.5% agarose gel. A fragment segregating with the phenotype was identified with +2 primer MseIntATC. (FIG. 2). The nested PCR was repeated with MseIntATC on all the individual plants (10 mu468 and 10 wild type). A perfect co-segregation was observed for a fragment 800nt. The co-segregating fragment was sequenced (SEQ ID NO: 26). A fragment-specific primer, 468R (5'-AGCTGCACCTTCGTCTCC) (SEQ ID NO: 27), was designed to pair with the MuTIR primers. Mutator insertion in the candidate gene was confirmed in family mu468, as well as two more independent mutant families, mu710 and mu453. The Mu insertions in these three lines are independent, though they are clustered within 50 bp.

Example 6

The Genomic Structure of the DLF1 Gene and cDNA

In order to obtain a genomic sequence of the DLF1 gene, BAC (Bacterial Artificial Chromosome) libraries were screened with the "over-go" probes designed for sequence of the Mu-adjacent fragment (SEQ ID NO: 26) that co-segregates with the DLF phenotype. 8 BAC clones were isolated. EcoR1 and HindIII fragments were subcloned from BAC's and 6836 nt were sequenced. The 3486-nt unique sequence (trimmed from retroelements on both sides) represents a complete copy of the DLF gene (SEQ ID NO: 1) (FIG. 3A).

To identify cDNA RT-PCR reaction was performed on mRNA isolated from the shoot apical meristem and the 1.3-kb-cDNA was isolated (SEQ ID NO: 2) (FIG. 3B). The fragment contains the 612-nt long ORF, which encoded putative protein of 204 amino acids. The EST (ACC #CB885390) from GenBank confirmed the polyA site at 550-nt downstream of the stop codon. Thus DLF1 produces RNA with a long 3'UTR. Alignment of the genomic DLF1 sequence and cDNA revealed one 80-nt intron (FIG. 3A).

A single HindIII band of the genomic DNA from inbred lines B73 and Mo17 hybridized with the DLF probe indicated that DLF1 is a unique single copy gene in the maize genome.

Example 7

Description of the Putative Protein Encoded by the DLF11 Gene

The sequence of the DLF1 gene encoded putative protein of 204 amino acids (SEQ ID NO:3). A homology search of the protein database such as EMBL-EBI, Swiss-Prot, GenBank revealed no protein matches indicating that DLF1 is a novel protein. According to InterProScan (Zdobnov E. M. and Apweiler R., (2001) "InterProScan—an integration platform for the signature-recognition methods in InterPro." Bioinformatics 17(9):847-8.) results, the DLF1 putative protein is annotated as a basic-leucine zipper (bZIP) transcription factor with a nuclear localization signal. The DLF1 protein contains a typical bZIP domain with a consensus region (Jakoby, et al., (2002) *Trends Plant Sci.* 7(3):106-11). A basic region between 133-156 amino acids includes an invariant DNA binding motif N-$x_7$-R/K followed by a heptad repeat of 3 leucines and valine. bZIP proteins bind to DNA as homo- or heterodimers (Jakoby, et al., (2002) *Trends Plant Sci.* 7(3): 106-11) that promoted by a leucine zipper. bZIP transcription factors are activated by phosphorylation at several sites (Siberil, et al., (2001) *Eur J Biochem.* 268(22):5655-66). Nine potential serine and one serine/threonine phosphorylation sites (FIG. 3B) were detected in the DLF1 protein (Blom, et al., (1999) *J Mol Biol.* 294(5):1351-62). Four sites are grouped at the N-terminus and four sites spread along the middle part, one site is located in the basic domain and one sites is located at the C-terminus. Thus it is likely that activity of DLF1 protein is modulated by phosphorylation like other bZIP transcription factors and it works in a signal transduction pathway (Siberil, et al., (2001) *Eur J Biochem.* 268(22): 5655-66).

Example 8

Sequencing of Reference EMS Alleles

To identify mutations in the ESM-induced reference alleles N2389A (SEQ ID NO: 34) and N2461 (SEQ ID NO: 35) (Neuffer M G, (1994) New mutant designation. MNL 68:28-29) a set of primers was designed to cover the coding region, 5' and 3'UTR of the DLF1 gene.

```
CGCCGACAGACATGTCGTCCTCGAGCAC    (SEQ ID NO: 28)

CATCTCCACGCAGCTGAGCCTCAACTCC;   (SEQ ID NO: 29)

TACTCGCTTTAGGAGAGCCTTTGACACG;   (SEQ ID NO: 30)

GTTCTGAGGACATTGACCGGAGATGAG;    (SEQ ID NO: 31)

ACCTGCTTCGACTCATCTCCGGTCAA;     (SEQ ID NO: 32)

GCGGTCTCTGGTGTCATTTGACCAGT      (SEQ ID NO: 33)
```

Sequence analysis of PCR products from the mutant N2389A has shown that this mutation is a transition from C to T that converted the CAG codon into the TAG stop codon terminating a protein at 88 amino acid (FIG. 3 and FIG. 4). The mutation N2461 is a transition from G to A, changing an arginine codon CGC to histidine codon CAG at position of 143 amino acid (FIG. 4). Arginine at position 143 is conserved throughout bZIP transcription factors (Siberil, et al., (2001) *Eur J Biochem.* 268(22):5655-66) indicating an indispensable function of arginine at position 143. Both mutations were induced by EMS that makes primarily transition mutation from GC>>AT, because it alkylates G at the O-6 position forcing a mispairing with T. Thus nucleotide changes of reference alleles are in agreement with EMS action.

Example 9

Phylogenetic Analysis of the DLF1 Protein

Extensive search of the GenBank sequence database revealed a single gene in the rice genome and one wheat EST encoded a complete DLF1-like protein. The rice DLF1-like protein (SEQ ID NO: 36) is a hypothetical protein predicted from the genomic sequence (GenBank accession #BAC79182, chromosome 9). A gene predicted by two or more gene prediction programs is classified as a 'hypothetical' protein according to IRGSP standard. The maize DLF1 (SEQ ID NO: 3) and rice DLF1-like proteins, share 48% identities, and 38% positives. The wheat EST (CK206464) encoded a complete DLF1-like protein (SEQ ID NO: 37) with a 612-nt coding region and a 500-nt long 3'UTR. The relative sizes of ORF and 3'UTR are similar to the maize DLF1 gene (651nt and 550nt respectively). The maize DLF1 and the wheat DLF1-like proteins, share 54% identities, and 40% positives.

The top hits to the *Arabidopsis* proteins have a homology around the position of 133-200 amino acids corresponding to a highly conserved basic leucine zipper domain in the DLF1 protein. *Arabidopsis* genome contains 75 putative genes encoding proteins with the bZIP signature (Jakoby, et al., (2002) *Trends Plant Sci.* 7(3):106-11). They have been divided into 10 groups according a similarity in the basic region and additional conserved motifs. Phylogenetic analysis performed with the PHYLUP program placed the monocot DLF1 proteins into a group A (FIG. 5). This group has 13 members in the *Arabidopsis* genome. Further analysis of all 13 members of the arabidopsis group A, related monocot bZIP proteins and DLF1 proteins delineated DLF1 in a subgroup with *Arabidopsis* genes AtbZIP14 (SEQ ID NO: 38) and AtbZIP27 (SEQ ID NO: 39) (FIG. 6). The amino acid alignment of 5 proteins from the DLF1 clade (FIG. 7) defined a serine-rich domain at the N-terminal end of the proteins, the highly homologues basic domain and 4 leucine in the zipper domain. The putative proteins share the similar number of phosphorylation sites indicating their participation in the signal transduction pathways.

Loss-of-function mutations in the *Arabidopsis* AtbZIP14 gene (named FD, according mutant phenotype, Flowering D) (GenBank acc #AB105818) cause delays in flowering time confirming that the DLF1 subgroup A of bZIP proteins in the floral transition in monocots and dicots.

Example 10

Expression Pattern of the DLF1 Gene in Different Tissues During Plant Development To determine the tissue specific expression of the DLF1 gene the LYNX expression database were queried with a putative DLF1 cDNA. The 17-mer tag GATCCCATGTTTT-TATT, positioned at 3'UTR (FIG. 3A) was found in the shoot apical meristem before and during the floral transition at 300-400 PPM (part per million) (FIG. 8A). The LYNX DLF tags were also present at 20-30 PPM in other tissues, including immature ears, root tip meristems, leaves. Electronic Northern is pointing to the shoot apical meristem as tissue where DLF1 is expressed at the highest level.

To confirm the in silico result, RNA was isolated from the shoot apical meristem of inbred lines B73, and reference EMS mutants N2389A (CR36 background) and N2461 (B73 background) at seedling stage (V3-V5). RNA gel blot hybridization (FIG. 8B) detected a transcript of the 1.2-bp long, that is consistent with a predicted transcript length (1.2-1.3 bp) from the genomic sequence (FIG. 3A). Thus, electronic and experimental Northerns confirmed that DLF1 is transcriptionally active in the shoot apical meristem and produced a transcript with a predicted length.

To understand the dynamic of the DLF1 expression during vegetative growth and transitioning to flowering, quantitative RT-PCR was conducted on RNA, isolated from the shoot apical meristems and immature leaves at different stage of seedling development (FIGS. 9 A and B).

DLF1 transcripts were accumulated in the SAM during vegetative growth reaching the high level of expression around the floral transition and decreasing to the non-detectable level after the transition. This pattern of expression is consistent with the DLF1 function as an activator of flowering.

DLF1 transcription is not self-regulated, because the gene is still transcribed in the DLF1-N2461 mutant background. (N2461 is a missense mutation that changed protein function).

Genetic analysis of the id1 and dlf1 double mutants was performed. So far there are only two cloned maize flowering mutants, id1 (Colasanti, et al, (1998) *Cell* 93(4):593-603)) and dlf1. Id1 is mapped to chromosomes and dlf1 is mapped to the bottom of chromosome 7. To assign these to genes to the flowering pathway double mutants were obtained by crossing heterozygous Id1/id1 and Dlf1/dlf1 plants. The preliminary analysis of the double mutants indicated that the Id1 gene is epistatic to the DLF1 gene because double id1/dlf1 mutants have the same phenotype as the id1/id1 single mutants. However, the transcription level of DLF1 gene in the id1 mutant background is affected only slightly (RT-PCR expression results, FIG. 9B) suggesting that the Id1 gene controls the function of the DLF1 gene at the protein level but not at the transcriptional level. The Id1 gene is the upstream regulator of the flowering pathway in maize and controls DLF1 and other down stream genes.

To detect photoperiod sensitivity of the DLF1 gene expression (FIG. 10), RT-PCR was conducted on RNA, isolated from immature leaves, the top green leaves, and the shoot apical meristem at seedling of V3 stage (vegetative growth) and V7 stages (just after the floral transition, B73 inbred line). Tissues were collected during 48 hrs to cover twice the day-night cycle with 8 hrs intervals) under the long day condition (16-hrs day and 8-hrs night, temperature 25° C.). In the SAM and immature leaves the level of DLF1 transcripts remains the same around the clock. However, in green leaves the DLF1 transcription is lower in the morning hours and increased afternoon and during the night. This data indicate that DLF1 gene is a photoperiod sensitive gene and might be partly under control of the circadian cycle in the green leaves.

Example 11

In Situ Localization of the Dlf1 Transcripts

To understand the pattern of DLF1 expression in the shoot apical meristem at both vegetative and reproductive stages of growth, in situ hybridization experiments were performed.

During vegetative growth, dlf1 transcripts accumulate within the rib zone of the shoot apical meristem and in cross-bands within the developing stem. The cross-bands seem to coincide with the point of attachment of the leaf primordia to the stem. No signal was detected in the central zone of the apical meristem or in the leaf primordia. During reproductive growth, dlf1 transcripts accumulate in the basal portion of the tassel primordium, the basal portion of the tassel branch primordia and the base of the leaf primordia. These data suggest that dlf1 function may be associated with transducing the floral signal to the apical meristem.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. An isolated polynucleotide selected from the group consisting of:
   (a) a polynucleotide having at least 95% sequence identity, as determined by the GAP algorithm under default parameters, to the full length sequence of the polynucleotide of SEQ ID NO:1; wherein expression of the polynucleotide in a plant delays flowering when compared to a control plant;
   (b) a polynucleotide encoding the polypeptide of SEQ ID NO:3;
   (c) a polynucleotide consisting of SEQ ID NO:1; and
   (d) a polynucleotide which is the full complement of any one of the polynucleotides of (a), (b), and (c).

2. A recombinant expression cassette, comprising the polynucleotide of claim 1, wherein the polynucleotide is operably linked, in sense orientation, to a promoter.

3. An isolated host cell comprising the expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut and cocoa.

8. A transgenic seed from the transgenic plant of claim 4.

9. A method of increasing yield in plants, comprising
   (a) introducing into a plant cell a recombinant expression cassette comprising the polynucleotide of claim 1, operably linked to a promoter; and
   (b) culturing the plant cell to produce a plant wherein the plant architecture is improved under plant cell growing conditions; wherein the yield is improved.

10. The method of claim 9, wherein the plant cell is from a plant selected from the group consisting of: maize, soybean, sunflower, sorghum, canola, wheat, alfalfa, cotton, rice, barley, millet, peanut and cocoa.

11. A method of increasing yield in a plant, comprising:
    (a) introducing into a plant cell a recombinant expression cassette comprising the polynucleotide of claim 1 operably linked to a promoter;
    (b) culturing the plant cell under plant cell growing conditions; and
    (c) regenerating a plant from said plant cell; wherein the plant architecture and yield are improved.

12. The method of claim 11, wherein the plant is selected from the group consisting of: maize, soybean, sorghum, canola, wheat, alfalfa, cotton, rice, barley, millet, peanut, and cocoa.

* * * * *

SEQUENCE LISTING

<160> NUMBER OF SEQ ID NOS: 39

<210> SEQ ID NO 1
<211> LENGTH: 3486
<212> TYPE: DNA
<213> ORGANISM: Zea mays

<400> SEQUENCE: 1

```
gactagttca agtaatttta tggttttgaa tttttcggag gctataatca ccctaatcca      60
atgagtctct acttacgcgc ttgctttccc cttaactcta caaatttctc gagtacctaa     120
gaaacactaa tatcgtcatg caacgacaat gttcatctaa tttttatgaa aaatttatgc     180
ctattggaca aatattaagg ttggatgaaa tagtgagaag ttaggacata attatggtca     240
cggttagttt taatgtatgt cccctccacg tctataactc ttcttttact agtagctaca     300
atatctaaaa cttacttgct ataactgagg gtataatatt cctatggaag tgttagtagc     360
ttgtgaactt tcttatggtt aaaactgtct atccatattt aacgtgattg gctgtttatt     420
tatttagtat tcattttaga gtcagcagtg atttagcgga gaaagggaga gtctggccaa     480
ttggcggtct ccggtgtcat ttgaccagtg ccaggtctca gtctgagtct atagtcaaca     540
gtgatctctc ggtcattggt tggcagtctc aggcacacac aatgacacaa cacaagcagg     600
gcacagtcac agtgtgagct gagctgagct gggcttgtgc ttgtgcttcc gcctcctcct     660
ccgcggctac taaagggtgc cagccagcca gccctgtggg gcgccggtgc gtgcccaaaa     720
caagcaagca taagcataga ggtgggcatc atagacatgg aggatgacga ggacatatgg     780
gcaaacaccg ccagcagccc cagcgcgtcc ccaccgcagc ccgtggcggc gggctcggtc     840
tccacctgca gcgccttcat ctccacgcag ctgagcctca actcccgcct ccacctcctc     900
tcctccgccg cggccggggg cgggtcctcc ccggtccgcg gcggcgccta cggcgcggac     960
ggtgtccgcc accaccacat ggctctcggc ggtggcttcc gcaatgccgc ggcgtcccag    1020
gggtcctcct ttccgtacaa cctcgccggc gccggcgccg atgtcgcgcc cttcgacggc    1080
ggccgcggcg tgctcgagga cgacatgtct gtcggcgccg ccgcgtccgg cacctgggct    1140
ggcgggggca ccgaccggcg gaagaagcgc atgatcaaga accgcgagtc cgccgcgcgg    1200
tcccgcgcgc gcaagcaggc gtacgtccgc gagctggaga cgaaggtgca gctgctgcag    1260
caggagaacg agagcctccg cgtcaagtac gacgaggtaa gcgggacatc gagagccccc    1320
ggcccttcat atatatggtc gctttgctca aagctcgcgc gtggattggg cagctgcggg    1380
agtccgtgga ggtggcggtg ccgatggtga ggaagaccct gcagaggatg ccgtccgcgc    1440
cgttctgagg acattgaccg gagatgagtc gaagcaggtg gttgctcgtt ttgtttgttt    1500
tttgaggagg tgattaagta agtgactgat tagtgagtgg ctgctgccta gtgcttggtt    1560
actagtagtg gtagaactca gaactacata gatccaggaa gcaagcaagc aaatccttcc    1620
tgccatggcg gcctcaatgt acatagatcc catgttttta ttaatttcgt ctagctgggg    1680
```

```
gggcgtgcac ctgccatggc ggcctccttt atttagcttt atataagtag gatgtaggat    1740
gtctaccata tgtgtgtagc ttgggattag gctgcaagaa gataagcctg cttgtacaaa    1800
tatggcttcc tggaacaatg acattttggg ggcgcaacgc aagaaagatg aaagaacaat    1860
ccaggaagca gcaggtgttt tcttcttctt cttcttttgc cccttccatg atattcgcgt    1920
gtcaaaggct ctcctaaagc gagtagtagt cttttggttt ggtgaatatt tgctgttttc    1980
atgctggtcc ctgctgatgt tgcgatgat tttacaatca gaaagagacg ttttttggtt    2040
ttgcctccat tctcttttg ttgctcagct tggcgaggg ggaaagccag taatttcgac    2100
gatagggaac aaaaaatgga tcgaattttg ggaccccttt gcttttctga agatggaac    2160
agaaggcaaa caaatcctga ctattgggag gatctaatttt tccttttttt agacaatgta    2220
gagcagctgc ttccctacac caggcaggag gcactggacc acagacacgc aaacagagct    2280
gcaagtctgc ctccccccaa gcaccctgct ccctccgatc taataactga ttttaataaa    2340
tcaatccatt aaagtttcac catatatata tatatatata tatatatata tatatgtaat    2400
gttgatattc attatacgag acaagtatca ttggattaat ctgaaaatgt attttttaac    2460
aataaataca ttaagagatg caaagttttt ttttttttt tgttctataa acctcaactt    2520
acttaattat atgattacat tctttctagg aataagtcta tatatataat ccctgtcgt    2580
ttgacatcat agaatgtcct ttgaaaatgg aagcttaacc ccctaacctt cataatgccg    2640
tatatagctg acaagatttt ctttgcttga gatcaagggt tacttaaggg atcacatgcc    2700
agttactgat ctactactgt tgcatcggtt gaagcctggg atgcagttag gtgatggatt    2760
ggttttgtta actgatgatg tgtcttgtaa aaaaatgtct gatcacacaa ccgatgcgcg    2820
gagtagcaga tgtgtatgtg gagggagtga atttgcaagc gaatgaatca tctgcatgtc    2880
tccttctaag gatccaaaag ttgacagcat gtttacaaat aaacaagaag aagtgaaagg    2940
agattcaggt aataaacagg gaaaagaaga tgaagagtgg tttggagatg tcagtgggga    3000
tgatgaagag gatgttggtt gcagtgatca tgagttacat ggtaaagatg aggaaggtag    3060
tagttcagat gaagaataca agcctccaga ggatgatagc tccacataag atgagggtca    3120
tgtgaaccaa gtggtttcta gttaatgggt catgtatgta aattaagtgc tttcatgtta    3180
agaaatggtt gtgatcttgc actttatgta ttccatagtt cacacaaaat aacattaata    3240
atacacgtta tatgtattgc actttaagaa atggttgtta tgttttttt gtctttatag    3300
agtataggta caacagttca aataattgac tttaatcaca agcgaacagt gatggatagg    3360
tatacggcaa agccctaatt tcctgtgaaa ctatatcgga gatattttg tgtactttgt    3420
tcaccagtgt atcggagata tttgatgttt ggtgtaccag agctgagcag cagtaatgaa    3480
ttcgat                                                               3486

<210> SEQ ID NO 2
<211> LENGTH: 1304
<212> TYPE: DNA
<213> ORGANISM: Zea mays

<400> SEQUENCE: 2
gcagtctcag gcacacacaa tgacacaaca caagcagggc acagtcacag tgtgagctga      60
gttgagctgg gcttgtgctt gtgcttccgc ctcctcctcc gcggctacta aagggtgcca     120
gccagccagc cctgtggggc gccggtgcat gcccaaaaca agcaagcata agcatagagg     180
tgggcatcat agacatggag gatgacgagg acatatgggc aaacaccgcc agcagcccca     240
```

```
gcgcgtcccc accgcagccc gtggcggcgg gctcggtctc cacctgcagc gccttcatct    300
ccacgcagct gagcctcaac tcccgcctcc acctcctctc ctccgccgcg gccggggcg     360 ggtcctcccc ggtccgcggc ggcgcctacg gcgcggacgg tgtccgccac caccacatgg    420
ctctcggcgg tggcttccgc aatgccgcgg cgtcccaggg gcccttcttt ccgtacaacc    480
tcgccggcgc cggcgccgat gtcgagccct cgacggcgg ccgcggcgtg ctcgaggacg     540
acatgtctgt cggcgccgcc gcgtccggca cctgggctgg cggggcacc gaccggcgga    600 agaagcgcat gatcaagaac cgcgagtccg ccgcgcggtc ccgcgcgcgc aagcaggcgt    660
acgtccgcga gctggagacg aaggtgcagc tgctgcagca ggagaacgag agcctccgcg    720
tcaagtacga cgagctgcgg gagtccgtgg aggtggcggt gccgatggtg aggaagaccc    780
tgcagaggat gccgtccgcg ccgttctgag gacattgacc ggagatgagt cgaagcaggt    840
ggttgctcgt tttgtttgtt ttttgaggag gtgattaagc aagtgactga ttagcgagtg    900
gctgctgcct agtgcttggt tactagtagt ggtagaactc ggaactacat agatctagga    960
agcaagcaag caaatccttc ctgccatggc ggcctcaatg tacatagatc ccatgttttt   1020
attaatttcg tctagctggg ggggcgtgca cctgccatgg cggcctcctt tatttagctt   1080
tatataagta ggatgtagga tgtctaccat atgtgtgtag cttgggatta ggctgcaaga   1140
agataagcct gcttgtacaa atatggcttc ctggaacaat gacattttgg gggcgcaacg   1200
caagaaagat gaaagaacaa tccaggaagc agcaggtgtt ttcttcttct tcttcttttg   1260 cccctccat gatattcgcg tgtcaaaggc tcaaaaaaaa aaaa                     1304
```

<210> SEQ ID NO 3
<211> LENGTH: 204
<212> TYPE: PRT
<213> ORGANISM: Zea mays

<400> SEQUENCE: 3

```
Met Glu Asp Asp Glu Asp Ile Trp Ala Asn Thr Ala Ser Ser Pro Ser
 1               5                  10                  15

Ala Ser Pro Pro Gln Pro Val Ala Ala Gly Ser Val Ser Thr Cys Ser
            20                  25                  30

Ala Phe Ile Ser Thr Gln Leu Ser Leu Asn Ser Arg Leu His Leu Leu
        35                  40                  45

Ser Ser Ala Ala Ala Gly Gly Gly Ser Ser Pro Val Arg Gly Gly Ala
    50                  55                  60

Tyr Gly Ala Asp Gly Val Arg His His His Met Ala Leu Gly Gly Gly
65                  70                  75                  80

Phe Arg Asn Ala Ala Ala Ser Gln Gly Pro Phe Phe Pro Tyr Asn Leu
                85                  90                  95

Ala Gly Ala Gly Ala Asp Val Glu Pro Phe Asp Gly Gly Arg Gly Val
            100                 105                 110

Leu Glu Asp Asp Met Ser Val Gly Ala Ala Ser Gly Thr Trp Ala
        115                 120                 125

Gly Gly Gly Thr Asp Arg Arg Lys Lys Arg Met Ile Lys Asn Arg Glu
    130                 135                 140

Ser Ala Ala Arg Ser Arg Ala Arg Lys Gln Ala Tyr Val Arg Glu Leu
145                 150                 155                 160

Glu Thr Lys Val Gln Leu Leu Gln Gln Glu Asn Glu Ser Leu Arg Val
                165                 170                 175

Lys Tyr Asp Glu Leu Arg Glu Ser Val Glu Val Ala Val Pro Met Val
            180                 185                 190
```

Arg Lys Thr Leu Gln Arg Met Pro Ser Ala Pro Phe
        195                 200

<210> SEQ ID NO 4
<211> LENGTH: 17
<212> TYPE: DNA
<213> ORGANISM: Artificial Sequence
<220> FEATURE:
<223> OTHER INFORMATION: Artificial sequence tag

<400> SEQUENCE: 4
gatcccatgt ttttatt                                                  17

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
tactcaggac tcatcgaccg t                                             21

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gtgaacggtc gatgagtcct gag                                           23

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ccaacgccaw sgcctcyatt tc                                            22

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
gtgaacggtc gatgagtc                                                 18

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
gcctcyattt cgtcgaatc                                                19

<210> SEQ ID NO 10
<211> LENGTH: 19

```
<212> TYPE: DNA
<213> ORGANISM: Artificial Sequence
<220> FEATURE:
<223> OTHER INFORMATION: primer

<400> SEQUENCE: 10
cgatgagtcc tgagtaaaa                                               19

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
cgatgagtcc tgagtaaac                                               19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
cgatgagtcc tgagtaaag                                               19

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
cgatgagtcc tgagtaaat                                               19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
cgatgagtcc tgagtaaca                                               19

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
gatgagtcct gagtaacc                                                18

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
```

```
gatgagtcct gagtaacg                                                 18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
gatgagtcct gagtaact                                                 18

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
cgatgagtcc tgagtaaga                                                19

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
gatgagtcct gagtaagc                                                 18

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
gatgagtcct gagtaagg                                                 18

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
cgatgagtcc tgagtaagt                                                19

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
cgatgagtcc tgagtaata                                                19

<210> SEQ ID NO 23
<211> LENGTH: 18
<212> TYPE: DNA
<213> ORGANISM: Artificial Sequence
```

```
<220> FEATURE:
<223> OTHER INFORMATION: primer

<400> SEQUENCE: 23
gatgagtcct gagtaatc                                                    18

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
gatgagtcct gagtaatg                                                    18

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
cgatgagtcc tgagtaatt                                                   19

<210> SEQ ID NO 26
<211> LENGTH: 810
<212> TYPE: DNA
<213> ORGANISM: Zea mays

<400> SEQUENCE: 26
gcctccattt cgtcgaatcc ccttccctct tcgtccataa tggcaattat ctctggagga      60
tgacgaggac atatgggcaa acaccgccag cagcccagc gcgtcccac cgcagcccgt      120
ggcggcgggc tcggtctcca cctgcagcgc cttcatctcc acgcagctga gcctcaactc    180
ccacctccac ctcctctcct ccgccgcggc cggggcggg tcctcccgg tccgcggcgg      240
cgcctacggc gcggacggtg tccgccacca ccacatggct ctcggcggtg gcttccgcaa    300
tgccgcggcg tcccaggggt ccttctttcc gtacaacctc gccggcgccg cgccgatgt    360
cgcgcccttc gacggcggcc gcggcgtgct cgaggacgac atgtctgtcg gcgccgccgc    420
gtccggcacc tgggctggcg ggggcaccga ccggcggaag aagcgcatga tcaagaaccg    480
cgagtccgcc gcgcggtccc gcgcgcgcaa gcaggcgtac gtccgcgagc tggagacgaa    540
ggtgcagctg ctgcagcagg agaacgagag cctccgcgtc aagtacgacg aggtaagcgg    600
gacatcgaga gccccggcc cttcatatat atggtcgctt tgctcaaagc tcgcgcgtgg    660
attgggcagc tgcgggagtc cgtggaggtg gcggtgccga tggtgaggaa gaccctgcag    720
aggatgccgt ccgcgccgtt ctgaggacat tgaccggaga tgagtcgaag caggtggttg    780
ctcgttttgt ttgttttttg aggaggtgat                                     810

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
agctgcacct tcgtctcc                                                    18
```

```
<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
cgccgacaga catgtcgtcc tcgagcac                                      28

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
catctccacg cagctgagcc tcaactcc                                      28

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
tactcgcttt aggagagcct ttgacacg                                      28

<210> SEQ ID NO 31
<211> LENGTH: 27
<212> TYPE: DNA
<213> ORGANISM: Artificial Sequence
<220> FEATURE:
<223> OTHER INFORMATION: primer

<400> SEQUENCE: 31
gttctgagga cattgaccgg agatgag                                       27

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
acctgcttcg actcatctcc ggtcaa                                        26

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
gcggtctctg gtgtcatttg accagt                                        26

<210> SEQ ID NO 34
<211> LENGTH: 88
<212> TYPE: PRT
<213> ORGANISM: Zea mays

<400> SEQUENCE: 34
```

```
Met Glu Asp Asp Glu Asp Ile Trp Ala Asn Thr Ala Ser Ser Pro Ser
1               5                   10                  15

Ala Ser Pro Pro Gln Pro Val Ala Ala Gly Ser Val Ser Thr Cys Ser
            20                  25                  30

Ala Phe Ile Ser Thr Gln Leu Ser Leu Asn Ser Arg Leu His Leu Leu
        35                  40                  45

Ser Ser Ala Ala Ala Gly Gly Gly Ser Ser Pro Val Arg Gly Gly Ala
    50                  55                  60

Tyr Gly Ala Asp Gly Val Arg His His His Met Ala Leu Gly Gly Gly
65                  70                  75                  80

Phe Arg Asn Ala Ala Ala Ser Gln
                85
```

<210> SEQ ID NO 35
<211> LENGTH: 204
<212> TYPE: PRT
<213> ORGANISM: Zea mays

<400> SEQUENCE: 35

```
Met Glu Asp Asp Glu Asp Ile Trp Ala Asn Thr Ala Ser Ser Pro Ser
1               5                   10                  15

Ala Ser Pro Pro Gln Pro Val Ala Ala Gly Ser Val Ser Thr Cys Ser
            20                  25                  30

Ala Phe Ile Ser Thr Gln Leu Ser Leu Asn Ser Arg Leu His Leu Leu
        35                  40                  45

Ser Ser Ala Ala Ala Gly Gly Gly Ser Ser Pro Val Arg Gly Gly Ala
    50                  55                  60

Tyr Gly Ala Asp Gly Val Arg His His His Met Ala Leu Gly Gly Gly
65                  70                  75                  80

Phe Arg Asn Ala Ala Ala Ser Gln Gly Pro Phe Phe Pro Tyr Asn Leu
                85                  90                  95

Ala Gly Ala Gly Ala Asp Val Glu Pro Phe Asp Gly Gly Arg Gly Val
            100                 105                 110

Leu Glu Asp Asp Met Ser Val Gly Ala Ala Ala Ser Gly Thr Trp Ala
        115                 120                 125

Gly Gly Gly Thr Asp Arg Arg Lys Lys Arg Met Ile Lys Asn His Glu
    130                 135                 140

Ser Ala Ala Arg Ser Arg Ala Arg Lys Gln Ala Tyr Val Arg Glu Leu
145                 150                 155                 160

Glu Thr Lys Val Gln Leu Leu Gln Gln Glu Asn Glu Ser Leu Arg Val
                165                 170                 175

Lys Tyr Asp Glu Leu Arg Glu Ser Val Glu Val Ala Val Pro Met Val
            180                 185                 190

Arg Lys Thr Leu Gln Arg Met Pro Ser Ala Pro Phe
        195                 200
```

<210> SEQ ID NO 36
<211> LENGTH: 207
<212> TYPE: PRT
<213> ORGANISM: Oryza sativa

<400> SEQUENCE: 36

```
Met Glu Asp Asp Glu Asp Met Trp Ala Asn Thr Ser Ser Pro Ser Ala
1               5                   10                  15

Ser Pro Pro Arg Pro Arg Gly Phe Ile Ser Thr Ala Leu Ser Leu Asn
            20                  25                  30
```

```
Ser Thr His Leu Gln Gly Leu Leu Pro Ser Ser Phe Val Asp Ala Ala
        35                  40                  45

Ala Ser Pro Cys His Ala Ser Gly Asn Asn Asn Gly Gly Gly Asp Gly
    50                  55                  60

Arg Asn Ala Ala Pro Met Ser Ser Ile Phe Phe Ala Ser Ala Ser Tyr
65                  70                  75                  80

His Gln Gln Gln His His Leu Pro Ala Pro Ala Pro Leu Asp Gly Ala
                85                  90                  95

Ile Leu Pro Ala Arg Arg Phe Gly Leu Asp Met Cys Ala Ala Ala Ala
            100                 105                 110

Ala Ala Pro Ala Gly Val Pro Ala Ala Gly Asp Arg Arg Lys Arg Arg
            115                 120                 125

Met Ile Lys Asn Arg Glu Ser Ala Ala Arg Ser Arg Ala Arg Lys Gln
            130                 135                 140

Ala Arg Val Asn Asn Leu Glu Thr Glu Val Glu Gln Leu Lys Gln Glu
145                 150                 155                 160

Asn Lys Met Leu Arg Val Lys Tyr Glu Gln Gly His Ser Gly Gln Trp
                165                 170                 175

Leu Glu Lys Pro Ser Leu Ala Arg Phe Ser Gln Met Ser Ile Phe Val
            180                 185                 190

Ser Pro Arg Ser Gly Tyr Val Ala Thr Leu Glu Arg Val Leu Met
            195                 200                 205

<210> SEQ ID NO 37
<211> LENGTH: 204
<212> TYPE: PRT
<213> ORGANISM: Triticum aestivum

<400> SEQUENCE: 37

Met Ala Met Glu Ala Asp Asp Asp Leu Trp Gly Ala Val Thr Thr
1               5                   10                  15

Ser Pro Ser Ala Ser Pro Pro Pro Ser Ser Ala Ala Ala Ile Ser
                20                  25                  30

Thr Ala Leu Ser Leu Asn Thr Arg Leu Gln Leu Leu Ala Ala Thr Gly
        35                  40                  45

Val Gly Gly Gly Ser Pro Phe His Pro Gly Val Gly Ala Gly Ser
    50                  55                  60

Pro Phe His Pro Gly Gly Gly Cys Tyr Arg Asn Gly Gly Ala Ser Pro
65                  70                  75                  80

Thr Ser Phe Phe Ser Ser Ala Ala Ser Phe Pro Arg Ile Ala Pro
                85                  90                  95

Val Asp Ala Gly Pro Ala Arg Arg Ala Leu Glu Arg Glu Met Cys Tyr
            100                 105                 110

Gly His Gly Ala Ala Ala Trp Pro Gly Ala Pro Gly Ala Gly Gly Gly
            115                 120                 125

Ala Ala Ala Pro Val Asp Arg Arg Lys Lys Arg Met Ile Lys Asn Arg
            130                 135                 140

Glu Ser Ala Ser Arg Ser Arg Ala Arg Lys Gln Ala His Val Thr Gln
145                 150                 155                 160

Ile Glu Ser Glu Val His Gln Leu Arg Glu Glu Asn Glu Gln Leu Arg
                165                 170                 175

Leu Lys Tyr Asp Gln Leu Lys Ala Ser Val Glu Val Ser Val Pro Val
            180                 185                 190

Arg Lys Thr Leu Gln Arg Val Leu Ser Ala Pro Phe
```

<210> SEQ ID NO 38
<211> LENGTH: 285
<212> TYPE: PRT
<213> ORGANISM: Arabidopsis thaliana

<400> SEQUENCE: 38

Met Leu Ser Ser Ala Lys His Gln Arg Asn His Arg Leu Ser Ala Thr
1               5                   10                  15

Asn Lys Asn Gln Thr Leu Thr Lys Val Ser Ile Ser Ser Ser
            20                  25                  30

Pro Ser Ser Ser Ser Ser Ser Thr Ser Ser Ser Pro Leu
        35                  40                  45

Pro Ser Gln Asp Ser Gln Ala Gln Lys Arg Ser Leu Val Thr Met Glu
    50                  55                  60

Glu Val Trp Asn Asp Ile Asn Leu Ala Ser Ile His His Leu Asn Arg
65                  70                  75                  80

His Ser Pro His Pro Gln His Asn His Glu Pro Arg Phe Arg Gly Gln
                85                  90                  95

Asn His His Asn Gln Asn Pro Asn Ser Ile Phe Gln Asp Phe Leu Lys
            100                 105                 110

Gly Ser Leu Asn Gln Glu Pro Ala Pro Thr Ser Gln Thr Thr Gly Ser
        115                 120                 125

Ala Pro Asn Gly Asp Ser Thr Thr Val Thr Val Leu Tyr Ser Ser Pro
    130                 135                 140

Phe Pro Pro Pro Ala Thr Val Leu Ser Leu Asn Ser Gly Ala Gly Phe
145                 150                 155                 160

Glu Phe Leu Asp Asn Gln Asp Pro Leu Val Thr Ser Asn Ser Asn Leu
                165                 170                 175

His Thr His His His Leu Ser Asn Ala His Ala Phe Asn Thr Ser Phe
            180                 185                 190

Glu Ala Leu Val Pro Ser Ser Ser Phe Gly Lys Lys Arg Gly Gln Asp
        195                 200                 205

Ser Asn Glu Gly Ser Gly Asn Arg Arg His Lys Arg Met Ile Lys Asn
    210                 215                 220

Arg Glu Ser Ala Ala Arg Ser Arg Ala Arg Lys Gln Ala Tyr Thr Asn
225                 230                 235                 240

Glu Leu Glu Leu Glu Val Ala His Leu Gln Ala Glu Asn Ala Arg Leu
                245                 250                 255

Lys Arg Gln Gln Asp Gln Leu Lys Met Ala Ala Ala Ile Gln Gln Pro
            260                 265                 270

Lys Lys Asn Thr Leu Gln Arg Ser Ser Thr Ala Pro Phe
        275                 280                 285

<210> SEQ ID NO 39
<211> LENGTH: 234
<212> TYPE: PRT
<213> ORGANISM: Arabidopsis thaliana

<400> SEQUENCE: 39

Met Leu Ser Ser Ala Lys His Asn Lys Ile Asn Asn His Ser Ala Phe
1               5                   10                  15

Ser Ile Ser Ser Ser Ser Ser Ser Leu Ser Thr Ser Ser Ser Leu Gly
            20                  25                  30

His Asn Lys Ser Gln Val Thr Met Glu Glu Val Trp Lys Glu Ile Asn

-continued

```
                35                  40                  45
Leu Gly Ser Leu His Tyr His Arg Gln Leu Asn Ile Gly His Glu Pro
     50                  55                  60
Met Leu Lys Asn Gln Asn Pro Asn Asn Ser Ile Phe Gln Asp Phe Leu
65                   70                  75                  80
Asn Met Pro Leu Asn Gln Pro Pro Pro Pro Pro Pro Pro Pro Ser Ser
                 85                  90                  95
Ser Thr Ile Val Thr Ala Leu Tyr Gly Ser Leu Pro Leu Pro Pro Pro
                100                 105                 110
Ala Thr Val Leu Ser Leu Asn Ser Gly Val Gly Phe Glu Phe Leu Asp
             115                 120                 125
Thr Thr Glu Asn Leu Leu Ala Ser Asn Pro Arg Ser Phe Glu Glu Ser
         130                 135                 140
Ala Lys Phe Gly Cys Leu Gly Lys Lys Arg Gly Gln Asp Ser Asp Asp
145                 150                 155                 160
Thr Arg Gly Asp Arg Arg Tyr Lys Arg Met Ile Lys Asn Arg Glu Ser
                165                 170                 175
Ala Ala Arg Ser Arg Ala Arg Lys Gln Ala Tyr Thr Asn Glu Leu Glu
             180                 185                 190
Leu Glu Ile Ala His Leu Gln Thr Glu Asn Ala Arg Leu Lys Ile Gln
         195                 200                 205
Gln Glu Gln Leu Lys Ile Ala Glu Ala Thr Gln Asn Gln Val Lys Lys
     210                 215                 220
Thr Leu Gln Arg Ser Ser Thr Ala Pro Phe
225                 230
```